(12) United States Patent
Subramaniam et al.

(10) Patent No.: US 9,727,032 B2
(45) Date of Patent: Aug. 8, 2017

(54) SYSTEMS AND METHODS FOR RUN-TIME SEQUENCING RUN QUALITY MONITORING

(75) Inventors: Yerramalli Subramaniam, Belmont, CA (US); Puneet Suri, Redwood City, CA (US); Sylvia Chang, Fremont, CA (US); Chengyong Yang, Foster City, CA (US)

(73) Assignee: Life Technologies Corporation, Carlsbad, CA (US)

(*) Notice: Subject to any disclaimer, the term of this patent is extended or adjusted under 35 U.S.C. 154(b) by 627 days.

(21) Appl. No.: 13/994,661

(22) PCT Filed: Dec. 6, 2011

(86) PCT No.: PCT/US2011/063495
§ 371 (c)(1),
(2), (4) Date: Aug. 28, 2013

(87) PCT Pub. No.: WO2012/082464
PCT Pub. Date: Jun. 21, 2012

(65) Prior Publication Data
US 2013/0331992 A1      Dec. 12, 2013

Related U.S. Application Data

(60) Provisional application No. 61/423,069, filed on Dec. 14, 2012, provisional application No. 61/424,481, (Continued)

(51) Int. Cl.
G05B 11/01 (2006.01)
G06F 19/22 (2011.01)

(52) U.S. Cl.
CPC ............. *G05B 11/01* (2013.01); *G06F 19/22* (2013.01)

(58) Field of Classification Search
CPC .................. G06F 19/22; G05B 11/01
See application file for complete search history.

(56) References Cited

U.S. PATENT DOCUMENTS

| 4,602,160 A | 7/1986 | MacTaggart |
| 4,648,714 A | 3/1987 | Benner et al. |

(Continued)

FOREIGN PATENT DOCUMENTS

| WO | WO-99/08233 | 2/1999 |
| WO | 2006/084123 | 8/2006 |

(Continued)

OTHER PUBLICATIONS

PCT/US2011/063495, "International Search Report and Written Opinion dated Jan. 8, 2012", 17 Pgs.

(Continued)

*Primary Examiner* — Shogo Sasaki

(57) ABSTRACT

Systems and methods of providing run-time quality control and monitoring of a single or multiple sequencing runs are provided herein. In some embodiments, the run-time system includes or is in communication with a processor capable of determining various types of run-time information relating to the quality, progress, etc. of various sequencing runs. In some embodiments, the system can also be in communication with a user interface, for example, a GUI, capable of representing and communicating various types of information to a user regarding the quality of the individual or multiple runs, the functioning of the instrument, an error event, etc. Additionally, the system can capable of receiving actionable information from a user via the GUI thereby allowing the user to terminate or repeat various sequencing steps in a particular run, terminate a entire run, terminate all runs, allow a run to proceed, etc.

20 Claims, 12 Drawing Sheets

Related U.S. Application Data filed on Dec. 17, 2010, provisional application No. 61/475,927, filed on Apr. 15, 2011.

(56) References Cited

U.S. PATENT DOCUMENTS

| | | | |
|---|---|---|---|
| 4,945,250 A | 7/1990 | Bowen et al. | |
| 5,149,972 A | 9/1992 | Fay et al. | |
| 6,075,643 A | 6/2000 | Nonoda et al. | |
| 6,274,320 B1 | 8/2001 | Rothberg et al. | |
| 6,414,805 B1 | 7/2002 | Reichman et al. | |
| 6,440,664 B1 | 8/2002 | Digby et al. | |
| 6,828,100 B1 | 12/2004 | Ronaghi | |
| 6,833,246 B2 | 12/2004 | Balasubramanian | |
| 7,211,390 B2 | 5/2007 | Rothberg et al. | |
| 7,223,363 B2 | 5/2007 | McNeely et al. | |
| 7,244,559 B2 | 7/2007 | Rothberg et al. | |
| 7,264,929 B2 | 9/2007 | Rothberg et al. | |
| 7,323,305 B2 | 1/2008 | Leamon et al. | |
| 7,335,762 B2 | 2/2008 | Rothberg et al. | |
| 7,381,569 B2 | 6/2008 | Woudenberg et al. | |
| 7,575,865 B2 | 8/2009 | Leamon et al. | |
| 7,835,871 B2 | 11/2010 | Kain et al. | |
| 7,948,015 B2 | 5/2011 | Rothberg et al. | |
| 2002/0051992 A1 | 5/2002 | Bridgham et al. | |
| 2002/0085293 A1 | 7/2002 | Stuckey | |
| 2003/0044879 A1 | 3/2003 | Beyer et al. | |
| 2004/0001196 A1 | 1/2004 | Shibazaki et al. | |
| 2004/0037739 A1 | 2/2004 | McNeely et al. | |
| 2004/0058450 A1 | 3/2004 | Pamula et al. | |
| 2004/0219688 A1 | 11/2004 | Churchill et al. | |
| 2005/0130188 A1 | 6/2005 | Walt et al. | |
| 2005/0151972 A1 | 7/2005 | Boege et al. | |
| 2006/0012860 A1 | 1/2006 | Bender | |
| 2006/0127939 A1 | 6/2006 | Woudenberg et al. | |
| 2007/0066931 A1 | 3/2007 | Kanamura et al. | |
| 2007/0195321 A1 | 8/2007 | Soussaline et al. | |
| 2007/0243634 A1 | 10/2007 | Pamula et al. | |
| 2008/0003571 A1 | 1/2008 | McKernan et al. | |
| 2008/0262747 A1* | 10/2008 | Kain | C12Q 1/686 702/20 |
| 2009/0149341 A1 | 6/2009 | Walt et al. | |
| 2010/0129810 A1 | 5/2010 | Greiner et al. | |
| 2010/0137166 A1* | 6/2010 | Kain | C12Q 1/686 506/39 |
| 2010/0138162 A1* | 6/2010 | Kain | C12Q 1/686 702/19 |
| 2010/0166612 A1 | 7/2010 | Lehto | |
| 2010/0323350 A1* | 12/2010 | Gordon | B01L 3/502761 435/6.16 |
| 2011/0009278 A1* | 1/2011 | Kain | C12Q 1/686 506/7 |
| 2011/0052446 A1 | 3/2011 | Hirano et al. | |
| 2011/0124111 A1 | 5/2011 | Hoshizaki et al. | |
| 2011/0128545 A1 | 6/2011 | Cox et al. | |
| 2011/0136677 A1 | 6/2011 | Oldham et al. | |
| 2011/0207624 A1 | 8/2011 | Shen et al. | |
| 2011/0246084 A1* | 10/2011 | Ronaghi | G06F 19/22 702/20 |

FOREIGN PATENT DOCUMENTS

| | | |
|---|---|---|
| WO | 2008/002502 | 1/2008 |
| WO | 2008/051310 | 5/2008 |
| WO | WO-2008/092150 | 7/2008 |
| WO | 2009/052095 | 4/2009 |
| WO | 2009/080766 | 7/2009 |
| WO | 2011/026136 | 3/2011 |
| WO | 2011/026141 | 3/2011 |

OTHER PUBLICATIONS

Margulies et al., Supplementary Methods for the article "Genome sequencing in microfabricated high-density picolitre reactors," *Nature*, 437:376-380 (2005), pp. 1-34.

Margulies et al., "Genome sequencing in microfabricated high-density picolitre reactors," *Nature*, 437:376-380 (2005).

* cited by examiner

SYSTEMS AND METHODS FOR RUN-TIME SEQUENCING RUN QUALITY MONITORING

CROSS-REFERENCE TO RELATED APPLICATIONS

This application is a U.S. National Application filed under 35 U.S.C. §371 of International Application No. PCT/US2011/063495, filed Dec. 6, 2011 which claims priority to U.S. Ser. No. 61/423,069, filed Dec. 14, 2010, U.S. Ser. No. 61/424,481, filed Dec. 17, 2010, and U.S. Ser. No. 61/475,927, filed Apr. 15, 2011, the disclosures of which are hereby incorporated herein by reference in their entirety as if set forth fully herein.

FIELD

The present disclosure relates to polynucleotide sequencing, and in particular to systems and methods for quality control monitoring of sequencing chemistry, instrumentation, etc. during a process.

INTRODUCTION

Nucleic acid sequence information can be an important data set for medical and academic research endeavors. Sequence information can facilitate medical studies of active disease and genetic disease predispositions, and can assist in rational design of drugs (e.g., targeting specific diseases, avoiding unwanted side effects, improving potency, and the like). Sequence information can also be a basis for genomic and evolutionary studies and many genetic engineering applications. Reliable sequence information can be critical for other uses of sequence data, such as paternity tests, criminal investigations and forensic studies.

Sequencing technologies and systems, such as, for example, those provided by Applied Biosystems/Life Technologies (SOLiD Sequencing System), Illumina, and 454 Life Sciences can provide high throughput DNA/RNA sequencing capabilities to the masses. Applications which may benefit from these sequencing technologies include, but are certainly not limited to, targeted resequencing, miRNA analysis, DNA methylation analysis, whole-transcriptome analysis, and cancer genomics research.

Sequencing platforms can vary from one another in their mode of operation (e.g., sequencing by synthesis, sequencing by ligation, pyrosequencing, etc.) and the type/form of raw sequencing data that they generate. However, attributes that are typically common to all these platforms is that the sequencing runs performed on the platforms tend to be expensive, take a considerable amount of time to complete, and generate large quantities of data.

SUMMARY

In various embodiments, as sequencing instrument can be in communication with a processor. The processor can monitor data received from the sequencing instrument, modify the operation of the sequencing instrument, provide information to an operator of the instrument, or combinations thereof. These and other features are provided herein.

Figure 1:
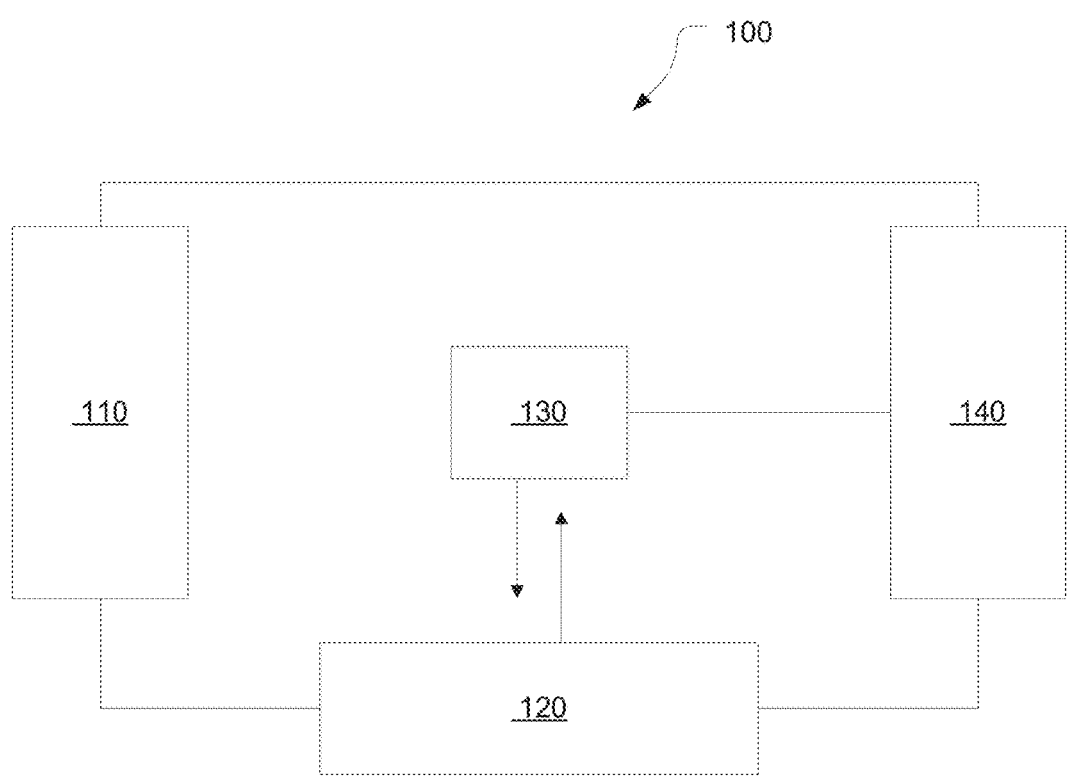
FIG. 1 depicts a block diagram representing various embodiments of instrumentation used for next generation sequencing.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts.

DESCRIPTION OF VARIOUS EMBODIMENTS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Unless otherwise defined, scientific and technical terms used in connection with the present teachings described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As utilized in accordance with the embodiments provided herein, the following terms, unless otherwise indicated, shall be understood to have the following meanings:

As used herein, "a" or "an" means "at least one" or "one or more".

The phrase "next generation sequencing" refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, pyrosequencing, and sequencing by hybridization. More specifically, the SOLiD Sequencing System of Life Technologies Corp. provides massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. Patent Publication No. 2011/0124111, entitled "Low-Volume Sequencing System and Method of Use," filed on Aug. 31, 2010, and U.S. Patent Publication No. 2011/0128545, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing experiment performed to determine some information relating to at least one biomolecule (e.g., nucleic acid molecule).

The phrase "ligation cycle" refers to a step in a sequence-by-ligation process where a probe sequence is ligated to a primer or another probe sequence.

The phrase "color call" refers to an observed dye color that results from the detection of a probe sequence after a ligation cycle of a sequencing run. Similarly, other "calls" refer to the distinguishable feature observed.

The phrase "synthetic bead" or "synthetic control" refers to a bead or some other type of solid support having multiple copies of synthetic template nucleic acid molecules attached to the bead or solid support. A linker sequence can be used to attach the synthetic template to the bead.

The phrase "fragment library" refers to a collection of nucleic acid fragments, wherein one or more fragments are used as a sequencing template. A fragment library can be generated, for example, by cutting or shearing, either enzymatically, chemically, or mechanically, a larger nucleic acid into smaller fragments. Fragment libraries can be generated from naturally occurring nucleic acids, such as bacterial nucleic acids. Libraries comprising similarly sized synthetic nucleic acid sequences can also be generated to create a synthetic fragment library.

The phrase "mate-pair library" refers to a collection of nucleic acid sequences comprising two fragments having a relationship, such as by being separated by a known number of nucleotides. Mate pair fragments can be generated by cutting or shearing, or they can be generated by circularizing fragments of nucleic acids with an internal adapter construct and then removing the middle portion of the nucleic acid fragment to create a linear strand of nucleic acid comprising the internal adapter with the sequences from the ends of the nucleic acid fragment attached to either end of the internal adapter. Like fragment libraries, mate-pair libraries can be generated from naturally occurring nucleic acid sequences. Synthetic mate-pair libraries can also be generated by attaching synthetic nucleic acid sequences to either end of an internal adapter sequence.

The phrase "synthetic nucleic acid sequence" and variations thereof refers to a synthesized sequence of nucleic acid. For example, a synthetic nucleic acid sequence can be generated or designed to follow rules or guidelines. A set of synthetic nucleic acid sequences can, for example, be generated or designed such that each synthetic nucleic acid sequence comprises a different sequence and/or the set of synthetic nucleic acid sequences comprises every possible variation of a set-length sequence. For example, a set of 64 synthetic nucleic acid sequences can comprise each possible combination of a 3 base sequence, or a set of 1024 synthetic nucleic acid sequences can comprise each possible combination of a 5 base sequence.

The phrase "control set" refers to a collection of nucleic acids each having a known sequence and physical properties wherein there is a plurality of differing nucleic acid sequences. A control set can comprise, for example, nucleic acids associated with a solid support. In some embodiments a control set can comprise a set of solid supports having a number of nucleic acid sequences attached thereto. Control sets can also comprise a solid support having a collection of nucleic acids attached thereto, such that each of the differing nucleic acid sequences is located at a substantially distinct location on the solid support, and sets of solid supports each having a substantially uniform set of nucleic acids associated therewith. The source of the nucleic acid sequences can be synthetically derived nucleic acid sequences or naturally occurring nucleic acid sequences. The nucleic acid sequences, either naturally occurring or synthetic, can be provided, for example, as a fragment library or a mate-pair library, or as the analogous synthetic libraries. The nucleic acid sequences can also be in other forms, such as a template comprising multiple inserts and multiple internal adapters. Other forms of nucleic acid sequences can include concatenates.

The term "subset" refers to a grouping of synthetic nucleic acid sequences by a common characteristic. For example, a subset can comprise all of the synthetic nucleic acid sequences in a control set that exhibit the same color call in a first ligation cycle.

The term "template" and variations thereof refer to a nucleic acid sequence that is a target of nucleic acid sequencing. A template sequence can be attached to a solid support, such as a bead, a microparticle, a flow cell, or other surface or object. A template sequence can comprise a synthetic nucleic acid sequence. A template sequence also can include an unknown nucleic acid sequence from a sample of interest and/or a known nucleic acid sequence.

The phrase "template density" refers to the number of template sequences attached to each individual solid support.

Run Monitoring

In various embodiments, a method for monitoring runtime information can include determining or evaluating an instrument or process related parameter. The parameter can be indicative of a status of a process or a portion thereof, a status of an instrument, a status of reagent, or any combination thereof. Additionally the status can relate to the quality of the process, the correct functioning of the instrument, expected versus actual performance of the process or instrument, or a combination thereof. Data from samples, data from controls, data from the instrument, or any combination thereof, can be monitored.

The data from the sample or control can include a signal, such as a fluorescent signal, a luminescent signal, a chemiluminescent signal, a measured current, voltage or resistance, a measured proton or ion concentration or generation, or other signals that can be used to identify nucleic acid sequence. The signal can be indicative of a probe coupled with a target sequence, a release of a pyrophosphate, proton, ion or other moiety indicative of the incorporation of a nucleotide or a ligation, the identity of a nucleotide or probe couple to the target sequence or incorporated into a complementary strand coupled to the target sequence, or any combination thereof. The data can include information about the intensity of the signal, the relative intensity of two or more signals, a signal quality value, or any combination thereof. For example, the quality value can be indicative of the confidence in the data, such as a probability the data is not the result of a random or chance event or otherwise false. Additionally, the data can include information about a color call, a base call, color separation, such as the ability is distinguish between multiple colors, correlation of the signal to a nucleotide, or combinations thereof. The data can also include information about the number of samples or a sample density, such as the number of samples per lane, panel, well, or other unit of the sample chamber.

Data from the instrument can include temperature, such as of the sample chamber or reagent storage area, pressure, such as within the fluid delivery system, reagent levels, instrument errors, other information indicative of the proper functioning of the instrument, or any combination thereof. Instrument errors can include, for example, errors indicative of instrument subcomponent malfunction, such as, for example, a manipulator, a stepper motor, a pump, or the like.

In various embodiments, runtime monitoring can be used for indentifying a performance or system issue, comparing the performance to past performance or a known standard, calibrating the instrument, monitoring test runs, or combinations thereof.

In various embodiments, the runtime monitoring can occur before, during, or after a run. Monitoring can occur one or more times during the sequencing run. Additionally, the monitoring can occur continuously throughout the sequencing run, such as, for example, continuous monitoring of an analog signal or frequent sampling of a digital signal. In particular embodiments, monitoring can occur by continuously monitoring a signal throughout specific portions of the sequencing run. Monitoring can occur at the beginning of the run, the end of the run, various points during the run, or any combination thereof. In particular embodiments, monitoring can occur when the samples introduced to the system, upon initiation of the sequencing cycle, upon completion of the sequencing cycle, upon initiation of a sequencing cycle, upon initiation of a ligation round, other points when the sample is manipulated or data is collected, or any combination thereof.

In various embodiments, data relating to the control can be compared to data relating to the sample. For example intensity of the signal for the control can be compared to the intensity of the signal for the sample. In other examples, the relative intensity or the quality of the sample signal can be compared to the relative intensity or the quality of the control signal. Significant deviations between the control data and the sample data, such as when the control signal intensity is high and the sample signal intensity is low, can be indicative of a problem with the sample.

Additionally, the runtime information can be used to compare performance versus historical performance or expected performance, such as a known standard or calculated control data. Data relating to the control can be compared to historical or calculated values. For example, when the same or similar controls are run repeatedly throughout the life of the instrument, deviations in the data relating to the control, such as the intensity, relative intensity, quality of the signal, can be indicative of an instrument or process related error. Similarly, data related to the sample can be compared to historical or expected values. Additionally, the control data can be compared to expected values. For example, color call, base call, or a correlation between a signal and a nucleotide can be compared to a known sequence for the control. If the color call or base call does not match the sequence, there may be a problem if the sequencing reaction or the reagents.

The data relating to the sample or the control can also be analyzed independently. For example intensity, relative intensity, or quality of the signal can be compared to a threshold or range of values. Values outside of the expected range can be indicative of process or instrument errors. Additionally, an error probability, such as a probability that the data is the result of a false signal or produced by random noise, can be calculated to evaluate the overall quality of the data. Further, the data can be analyzed to evaluate the ability to identify or distinguish signals. For example, the data can be analyzed to evaluate an intensity resolution or sensitivity, a spatial resolution, a color separation, signal to noise ratio, or the like. In particular embodiments, color separation can be analyzed using a satay graph. The data can be compared to an expected pattern. Additionally, the number of data points that fall outside of an expected region or a measure of this spread of the data points can be calculated. Further, the probability that an individual data point is the result of random noise can be determined. Additionally, the number of data points that fall outside of an expected region or data that has a high probability of being produced by random noise can be determined and can be compared to a threshold or range of acceptable or expected values.

Runtime monitoring can provide an assessment of the overall quality of the data produced during sequencing run. For example, the assessment of the data can be provided to an operator to enable the operator to further evaluate the quality of the sequence. In a particular embodiment, an overall indicator of run quality can be provided to the operator. For example, and indicator showing green can indicate a good overall quality, an indicator showing yellow can indicate a diminishing overall quality, and an indicator showing red can indicate an overall quality insufficient to accurately determine the sequence of the nucleic acid sample. Additionally, more detailed information can be provided to the operator to further understand the factors affecting the overall data quality. For example, the operator can be provided access to satay graphs for the assessment of the color separation.

Additionally, the operator can have access to heat maps, false color graphs or images in which the color is related to the value of the parameter in that region. In various examples, the heat map can indicate a change in a value at various locations within a sample chamber or over time, such as across consecutive ligation cycles. Exemplary parameters that can be displayed in a heat map can include the number of incorrect color or base calls for the control, the number of samples with a low quality value or high error probability, average signal intensity for a region, sample density for a region, and the like. The operator can use the heat maps to identify portions of the sequencing run, such as regions within a sample chamber or particular time periods, where the quality of the data may be diminished.

In various embodiments, the operator can be various indications of the number of targets such as beads or wells with an associated target nucleic acids. For example, a focal map can be provided indicative of the location of target nucleic acids with a sample holder. For example, the sample map can be determined by coupling one or more probes with the target nucleic acids and identifying locations where there is a high concentration of probes, such as locations that produce a high probe signal. In another example, a deposition profile can be provided. The deposition profile can be indicative of the number of identifiable locations compared to a predetermined limit. In particular embodiments, the deposition profile can be displayed as a heat map showing regions with high, intermediate, and low useable beads. The deposition profile or focal map can be usable to distinguish between low usable locations due to low sample loading or high sample loading. Specifically, when the sample loading is too high, samples may overlap, thereby reducing the number of usable locations.

In various embodiments, runtime monitoring can identify problems that occur during sequencing run. For example runtime monitoring may provide an indication of data quality, such as identifying when the data obtained may be insufficient to reliably determine the color sequence or nucleotide sequence. Additionally, the runtime monitoring can identify a potential cause of the problem. For example runtime monitoring may distinguish between problems caused by instrument errors, chemistry issues, reagents, or sample preparation. Runtime monitoring can notify the operator when the data quality becomes unacceptable, such as when the data is insufficient for a nucleotide or color call for a significant portion of the sample. When the data quality becomes unacceptable, the runtime monitoring can notify the operator, perform actions to minimize the impact of the problems, or combinations thereof. For example, the operator may be notified when the number of uncalled samples exceeds a threshold, increases rapidly, or is outside of an expected range. In another example, the operator can be notified when the number of controls with incorrect color calls or nucleotide calls exceeds a threshold, increases rapidly, or is outside of an expected range.

The operator can be notified by electronic message, such as an e-mail an SMS message, MMS message, a numeric page, or combinations thereof, by an audible of alert, such as a tone or alarm, the phone call, or the like, by a visual display, such as an on-screen error message, or by combinations thereof. Additionally, the sequencing reaction can be paused pending further operator input, the sequencing reaction can be terminated, portions of the sequencing reaction can be repeated, or combinations thereof. In particular embodiments, a sequencing reaction can be terminated for a portion of the sample chamber, such and for one of a set of flow cells, a lane of a flow cell, or combinations thereof. Portions of the sequencing run can be repeated when the problem may be recoverable, such as a temporary issue. Alternatively, when the problem is determined to be unrecoverable, for example, after repeating the same portion of the sequencing run without improvement or the problem is attributed to the sample preparation, the sequencing reaction may be terminated.

Run Control

In various embodiments, a method for run control can change a reaction or system condition, such as based on a quality control parameter, a predetermined event, an operator input, or combinations thereof. For example, portions of the sequencing run can be repeated, the number of ligation rounds can be reduced, the sequencing run can be paused or terminated, reagent delivery can be altered, or combinations thereof. Conditions can be changed to improve or maintain system performance, or to reduce the amount reagents or instrument time used. For example, when a read length prediction indicates later portions of a sequencing cycle are unlikely to provide data of sufficient quality the read length can be reduced to save instrument time or reagents.

Run control can occur once or multiple times during a sequencing run. Changes to the reaction or system conditions can occur at the beginning of the sequencing run, at various times during the sequencing run, or combinations thereof. The changes can occur in an automated fashion, such as in response to a preprogrammed trigger, or in response to an operator input. Additionally, the operator can be notified when a trigger event occurs. The trigger event can include a change in the quality control parameter, a scheduled time, or combinations thereof.

GUI

In various embodiments, a graphical user interface (GUI) can be provided to enable the interaction of an operator with a runtime monitoring system or a run-time control system. The GUI can be configured to provide information relating to the runtime monitoring of a sequencing instrument. In particular embodiments, the GUI can provide various indications of data quality. For example, the GUI can provide satay maps, heat maps, assessment of the data quality and runtime performance, other indications and assessments of the data collected by the sequencing instrument, or combinations thereof. Additionally, the GUI may provide status information relating to the sequencing run. For example, the GUI can provide an indication of a current activity of the sequencing in front instrument, an estimation of when the sequencing reaction run will be completed, upcoming events, such as when reagents will need to be replaced, past events, such as when the sequencing run is initiated, pause, or altered, and combinations thereof. The GUI can be configured to receive information from the operator and to perform actions based on the information. For example, the GUI can be configured to enable the operator to configure a sequencing run, schedule events, configure actions to be performed in response to runtime monitoring, alter a sequencing run, or combinations thereof.

Remote Device

In various embodiments, the processor can be in communication with a remote device, such as a client system, a portable or handheld device, or the like. Examples of portable or handheld devices can include smart phones, tablets, portable digital assistants (PDAs), and the like. The processor can send a notification to the remote device, such as when a problem is detected or a trigger event occurs. Additionally, the processor can provide access to information, such as heat maps, satay plots, and other information the operator may find useful, to the operator through the remote device. Additionally, the operator can provide input to the processor through the remote device. In particular embodiments, the remote device can provide substantially all of the functionality of the GUI or a subset thereof to the operator.

In various embodiments, the processor may provide access through a web interface, a client application running on the remote device, a remote terminal session, or the like. Additionally, communication between the processor and the remote device can be authenticated, encrypted, or a combination thereof, to prevent unauthorized access to the data or control of the sequencing instrument. Examples of authentication can include user specific authentication, such as usernames, passwords, biometrics, and the like, device specific authentication, such as device identifiers, keys, tokens, and the like, or any combination thereof.

Instrument

Various embodiments of platforms for next generation sequencing can include components as displayed in the block diagram of FIG. 1. According to various embodiments, sequencing instrument 100 can include a fluidic delivery and control unit 110, a sample processing unit 120, a signal detection unit 130, and a data acquisition, analysis and control unit 140. Various embodiments of instrumentation, reagents, libraries and methods used for next generation sequencing are described in U.S. Patent Application Publication No. 2007/066931 and U.S. Patent Application Publication No. 2008/003571, which applications are incorporated herein by reference. Various embodiments of instrument 100 can provide for automated sequencing that can be used to gather sequence information from a plurality of sequences in parallel, i.e., substantially simultaneously.

In various embodiments, the fluidics delivery and control unit 110 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 120 can include a sample chamber, such as flow cell, a substrate, a micro-array, a multi-well tray, or the like. The sample processing unit 120 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 130 can include an imaging or detection sensor. For example, the imaging or detection sensor can include a CCD, a CMOS, an ion sensor, such as an ion sensitive layer overlying a CMOS, a current detector, or the like. The signal detection unit 130 can include an excitation system to cause a probe, such as a fluorescent dye, to emit a signal. The expectation system can include an illumination source, such as arc lamp, a laser, a light emitting diode (LED), or the like. In particular embodiments, the signal detection unit 130 can include optics for the transmission of light from an illumination source to the sample or from the sample to the imaging or detection sensor. Alternatively, the signal detection unit 130 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 140 can monitor various system parameters. The system parameters can include temperature of various portions of instrument 100, such as sample processing unit or reagent reservoirs, volumes of various reagent, the status of various system subcomponents, such as a manipulator, a stepper motor, a pump, or the like, or any combination thereof.

It will be appreciated by one skilled in the art that various embodiments of instrument 100 can be used to practice variety of sequencing methods including ligation-based methods, sequencing by synthesis, single molecule methods, nanopore sequencing, and other sequencing techniques. Ligation sequencing can include single ligation techniques, or change ligation techniques where multiple ligation are performed in sequence on a single primary. Sequencing by synthesis can include the incorporation of dye labeled nucleotides, chain termination, ion/proton sequencing, pyrophosphate sequencing, or the like. Single molecule techniques can include continuous sequencing, where the identity of the nuclear type is determined during incorporation without the need to pause or delay the sequencing reaction, or staggered sequence, where the sequencing reactions is paused to determine the identity of the incorporated nucleotide.

Sample/Control

In various embodiments, the sequencing instrument 100 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 100 can obtain the sequence information from a single nucleic acid molecule or from a group of substantially identical nucleic acid molecules.

The sequencing instrument 100 can operate on a sample, a control, or a combination thereof. The sample can include a nucleic acid with an unknown sequence. The control can include a nucleic acid with a known sequence, and can include or be derived from a synthetic or natural nucleic acid. The sample or control nucleic acid can be attached to a solid or semi-solid support. Examples of a support can include a bead, a slide, a surface of a flow cell, a matrix on a surface, a surface of a well, or the like. In particular embodiments, the surface may include multiple nucleic acids with a substantially identical sequence grouped together. For example, a bead can have a population of substantially identical nucleic acids. The sequencing instrument may determine sequence information from multiple beads simultaneously in a parallel fashion. In another example, a surface can be populated with multiple clusters of nucleic acids, with each cluster including a population of substantially identical nucleic acids.

Processor

In the various examples and embodiments described herein, a system for sequencing nucleic acid samples can include a sequencing instrument and a processor in communication with the sequencing instrument. In some embodiments, sequencing instruments can be in communication with other sequencing instruments as well as with processors, and processors can be in communication with other processors as well as with sequencing instruments. Communication between and among sequencing instruments and processors can take many forms known the skilled artisan, including direct or indirect and physical, electronic/electromagnetic), or otherwise functional (e.g., information can be transferred via wires, fiber optics, wireless systems, networks, internet, hard drives or other memory devices, and the like).

In various embodiments, the processor can include a Central Processing Unit (CPU), such as a coreDuo, a Nehalem, an Athlon, an Opteron, a PowerPC, or the like, a Graphics processing unit (GPU), such as the GeForce, Tesla, Radeon HD, or the like, an Application-specific integrated circuit (ASIC), a Field programmable gate array (FPGA), or the like. In various embodiments, the processor can include a single core processor or a multi-core processor. Additionally, multiple processors can be coupled together to perform tasks in parallel. The processor can be incorporated into the computer system, such as a server system or client system, such as desktop or laptop, or a mobile or handheld system, such as a PDA, smartphone, tablet, or the like. The computer system can be a general purpose computer, such as a general-purpose computer program performs specific functions, or a special-purpose computer.

The processor can be configured to store or access data, such as expected information. The expected information can include information about known or control sequences, such as nucleotide sequences, sequences of color calls, or the like. The known or control sequences can be stored in a table or other query-able form. Additionally, the expected information can include expected system parameters, such as thresholds for system parameters, ranges of expected values, expected changes to the system parameters over time, or combinations thereof. Additionally, the processor can be configured to receive data inputs from a sequencing instrument. The data inputs can include system parameters, data relating to the control, data relating to the sample, and combinations thereof.

The processor can be configured to compare data received from a sequencing instrument to expected data. For example, the processor can compare data relating to the control to a known sequence for the control. The processor can compare data such as a color call, nucleotide call, or the like for an individual position to the known sequence without reference to preceding or subsequent positions, or data for multiple positions. Additionally, the processor can be configured to compare data, such as quality values, intensity, relative intensity, and the like of a control to a sample. The processor can be configured to compare data from the sequencing instrument from a prior run to a current run. Additionally, the processor can be configured to compare system parameter data received from the sequencing instrument to expected system parameter.

The processor can be configured to provide information to an operator, such as information related to call quality, intensity of a signal, relative intensity, status of the instrument or a sequencing run, needed reagents, and the like. The processor can be configured to display quality information, such as an overall quality indicator and specific quality information, such as a heat map, a satay graph, or the like. Additionally, the processor can be configured to display run status or reagent information. The run status can include an estimated completion time, a current status, such as paused, running, or stopped, current activity, or combinations thereof. The reagent information can include levels of various reagents, an estimated time for adding or replacing reagents, or combinations thereof.

In various embodiments, processors can be incorporated into quality control systems for sequencing instruments. In some embodiments, processors can provide run monitoring, such as by monitoring various aspects of sequencing instruments including operating parameters, data produced by sequencing instruments, or any combination thereof. In some embodiments, processors can provide run control. Processors can cause a modification of the operation of the sequencing instrument.

In some embodiments, a processor can receive sequencing data from a sequencing instrument. For example, the sequencing data can include image data, color signals, color calls, sequence information, or other data generated at various points during the sequencing analysis. Additionally, the sequencing data can include data for control sequences, sample sequences, or any combination thereof. The processor can receive the sequencing data at the beginning of a sequencing run, the end of a sequencing run, or at various times during the sequencing run, such as for each ligation cycle. The processor can monitor the sequencing data to ensure the quality of the sequence information produced by the sequencing instrument. For example, the processor can compare color calls of the control sequences to expected color calls for the control sequences. Additionally, processors can compare color signals of the control sequences to a history of various runs performed by the instrument. Further, the processor can compare the color signals of the sample sequences to the color signals of the control sequences.

In some embodiments, a processor can also receive operating data from a sequencing instrument, such as temperature of the flow cell, pressure within the fluid delivery system, reagent volume, or any combination thereof. Those skilled in the art would recognize that the processor can receive and monitor additional operating data that can affect the operation and performance of the sequencing instrument. The processor can receive the operating data from the sequencing instrument continuously, periodically, or at particular times during the sequencing run. Those skilled in the art would recognize that continuously can include receive a continuous analog signal representing the operating parameter or discrete values taken at a sufficiently high sampling frequency, such as, for example, at least once per minute, at least once per 10 seconds, at least once per second, at least once per tenth of a second, or even higher sampling frequencies. The processor can monitor system parameters with respect to predetermined thresholds or ranges.

In some embodiments, a processor can provide run control to alter the operation of the sequencing instrument. The processor can alter the operation of the sequencing instrument to minimize waste of resources such as reagents or time, improve or maintain performance during a sequencing run, or any combination thereof. Run control can be provided in response to operator input, prescheduled events, reaction or system conditions, or any combination thereof. In some embodiments, when the sequencing data falls outside of expected parameters, such as when sample color signals fall relative to the control color signals, the processor can perform various event handling routines. For example, the processor can notify an operator, pause a sequencing run, repeat a portion of a sequencing run, or otherwise minimize resources, such as time and reagents, expended obtaining sequencing data of insufficient quality. In some embodiments, when system parameters cross a threshold or move outside of acceptable ranges, the processor can perform various event handling routines. The processor can be configured to provide run control a various times during the sequencing run. For example, the processor can be configured to establish a set of operating parameters at the beginning of the sequencing run, change the operation of the sequencing instrument during the run, or any combination thereof.

In some embodiments, the processor can be configured to provide run time information to a user via, such as for example, through a Graphical User Interface (GUI). In some embodiments, the system can be configured to receive input from the user (e.g., via the GUI) such that the user can instruct the system to terminate, repeat, or maintain certain procedures or sequences due in part to signals received from the system via the GUI (or some other output/user interface component).

In various embodiments, the processor can receive quality data from the sequencing system in various manners in order to determine a particular quality metric or metrics. For example, in some embodiments, the sequencing system can run a sequencing procedure in parallel with a control procedure thereby allowing for a comparison between results of the sequencing and the control processes. For example, in some embodiments, the sequencing system can include various control compositions (e.g., synthetic polynucleotides of known sequence) inter-mixed (or other-wise associated) in some manner with samples to be sequenced. For example, in some embodiments, the sequencing system can include a plurality of samples to be sequenced disposed, positioned, grown, or otherwise distributed on or relative to a substrate and run-time monitoring system can continuously and/or regularly monitor and/or compare the quality of sequencing data arising from the unknown samples relative to the quality of data from the know, control data and from this comparison determine some type of run-time control information which can be presented to the user via the GUI in a manner indicative of the status of the run. In some embodiments, the run-time system and utilize this comparison to generate run-time information which can serve as a control for the validation, calibration, and/or normalization of instrumentation, chemistry (e.g., probe chemistry), methods, process, and compositions used in genetic analysis.

The run-time system can be configured to determine and/or output various amounts and/or types of information in various formats. For example, in some embodiment, the system can output various type of information via, for example, a GUI which indicate how the run is progressing, how each run in each channel of a flowcell is progressing, whether a user needs to take any action, suggested action a user could be taking, and identification of various other types of problems or issues.

For example, in some embodiments, the run-time system can be configured to provide a visual display of the substrate on which the sequencing runs are being performed. For example, in those embodiments utilizing a flowcell having various channels wherein distinct or the same sequencing runs are being performed in each channel, the run-time system can be configured to provide the user with a visual representation of a flowcell (or multiple flowcells if there are more than one flowcell present) via a GUI. In some embodiments, the visual representation provides the user with quick and reliable information relating to the quality and/or status of each sequencing run taking place in each individual channel. For example, each channel where there are no issues can be represented as "green" and channels where there are potential issues can be represented as "orange," and channels where there is a clear issue can be represented as "red." In some embodiments, the representation can also provide a user with immediate information regarding how long each run has been progressing, when the run should be completed, and scheduled pauses in the run, etc. Such information can be conveyed in various manners. For example, in some embodiments, the each channels can change color moving, for example, left to right as the run proceeds from left to right across a channel. In some embodiments, the sequencing quality can be superimposed relative to a quality threshold value such that a user can monitor the actual quality versus the threshold quality. Thus, in some embodiments, the user can monitor the easily monitor the progress of a reaction relative to a desired threshold and immediately know if quality is decreasing relative to the threshold, maintaining constant, improving, etc. In some embodiments, various bar-graphs can be displayed relative to a threshold value. In some embodiments, the system can signal an event if some predetermined quality control metrics fail to reach the desired quality threshold, such as for example over a consecutive number of cycles or rounds.

In some embodiments, processors can provide a graphical user interface ("GUI") in communication with a large-scale sequencing system wherein the GUI is in communication with a processor configured to implement monitoring or quality control analysis of any of a number of sequencing runs (or some step(s) of a sequencing run) being performed on a sequencing platform. The systems and methods provided herein can include various types of information regarding various steps of any number of runs being performed on the system. For example, the system can provide a time-status update, a quality-control update, a failure notification update, a reagent update, etc.

Additionally, systems can also be configured to receive user-feedback via the GUI (or some other mechanism). For example, in response to a failure notification, the user can instruct the system via the GUI (or some other user-interface) to terminate a particular run taking place within a particular location of the substrate (e.g., within a first channel of the flowcell). In some embodiments, the user can instruct the system to repeat some step of the sequencing process due to unsatisfactory results. In some embodiments, the user can instruct the system to repeat the entire (or at least some steps of the) protocol or the user can instruct the system to perform various steps in certain areas of the substrate (i.e., within a first channel) while performing other steps (or merely allowing the protocol to move forward) in other areas of the substrate (e.g., other channels of the flowcell).

In some embodiments, systems can also be configured such that the GUI can display run-time information relating to reagent usage, reagent identities, etc. For example, in some embodiments, the run-time system can be programmed such that upon initiation or selection of a certain protocol to run (e.g., user selects protocol "A" to be run in channel 1 of flowcell "A"), the GUI can display the identify and volumes of all reagents needed for that run, confirm that such reagents are present in the necessary volumes, confirm that such reagents have passed quality control procedures, and/or provide any other information deemed useful or necessary. In some embodiments, the system can be configured such that upon initiation of a run, the GUI determines and identifies various pause points wherein a sequencing run will pause to allow a user to check on reagent volumes and/or replenish some or all of the reagents, etc.

In some embodiment, the run-time system can be configured to determine and/or provide more detailed information relating to each run proceeding in each individual channel. For example, the system and/or GUI (or other user interface) can be configured such that a user can merely input a channel identifier (e.g., channel 1 of flowcell A) or scroll over a certain channel of a flowcell of a certain area of a flowcell to receive additional, detailed information relating to the sample and/or receive various quality metrics relating to that run at the selected position. In some embodiments, the user can also receive specific information regarding a specific library by inputting to the GUI or selecting from the GUI a sample identifier (e.g., a particular barcode indicative of a sample).

Once a particular channel or sample has been selected, the system can be configured in various manners to provide various detailed information regarding the particular channel or sample selected. For example, the run-time system can provide a representation of the quality of the sequencing data arising from each channel. For example, in some embodiments, the system can be employed with the SOLiD Sequencing System of Life Technologies (Carlsbad, Calif.) wherein a ligation chemistry protocol results in numerous color signals being generated during various steps of a run. IN general, the system generates one of four possible color calls which correspond to four possible fluorescent dyes taking part in various ligation reactions. While these dyes by themselves do not provide a user with information relating to a base sequence (which is not provided until the end of the run), the quality of the color signals can provide an indication as to the quality of the run. Thus, in some embodiments, the run-time system can provide run-time analysis and representation of the quality (e.g., ability to distinguish one color from another) of these color calls. For example, in some embodiments the system can be configured to provide a visual representation to a user of a Satay chart wherein a value of each color generated is represented along a distinct axis of the chart. In some embodiments, the run-time system is configured to provide a pie-chart wherein each signal is represent by one of four section of the chart.

As detailed in Assignee's co-pending U.S. Patent Publication Nos. 2010/0129810 and 2011/0207624 the entirety of these applications being incorporated herein by reference, in some embodiments, various control mechanisms can be incorporated into a sequencing run wherein the mechanisms can be configured to indicate quality (or lack thereof) of some sequencing run. In some embodiments, the presently disclosed system can collect run-time signal information from a sample being sequenced as well as run-time signal information from a corresponding control mechanism (e.g., control samples within a proximity, "group," or same area) as the sample. The system can then be configured to compare this data in some manner and, through this comparison, generate a quality value or other metric relating to the run. In some embodiments, the system can be configured to provide a graphical representation of the quality of such data or runs on the GUI (or other user interface) such that a user can make run-time decisions about allowing the run to continue, terminating the run, continuing a portion of the run, etc. The ability to easily display and represent such quality-value information allows a user to save time and also prevent reagent waste should a termination decision be made early in a run as opposed to allowing the run to proceed to completion.

As indicated above, the run-time sequencing system can be utilized with various sequencing systems and/or platforms having various components. In some embodiments, the system can include a sequencing instrument and a processor in communication with the sequencing instrument. As indicated above, in some embodiments, the sequencing instrument can be configured to interrogate a control set and a nucleic acid sample and produce control data for the control set and sample data for the nucleic acid sample. In some embodiments, the run-time system can be in communication with the processor of the system (or be the same processor) and can be configured to obtain the control data and the sample data from the sequencing instrument, determine a control quality value for the control data and a sample quality value for the sample data, and compare the control quality value, the sample quality value, and a threshold. As indicated above, the processor can be further configured to perform an event handling routine when the control quality value or the sample quality value is below the threshold.

In some embodiments, a computer program product can include instructions to obtain control data and sample data from a sequencing instrument, instructions to determine a control quality value for the control data and a sample quality value for the sample data, and instructions to perform an event handling routine when the control quality value or the sample quality value is below a threshold.

In some embodiments, a method can include obtaining the control data and the sample data from a sequencing instrument, determining a control quality value for the control data and a sample quality value for the sample data, and performing an event handling routine when the control quality value or the sample quality value is below a threshold.

In some embodiments, a computer program product can include instructions to determine a total time or time points for sequencing a nucleic acid sample by a sequencing instrument, and instructions to display a graph indicating the duration. The graph may be a timeline or other indication of progress through the sequencing run, such as indicating the various sequencing cycles. The computer program product can further include instructions to monitor the process of the sequencing and display the progress on the graph, instructions to determine a data quality for the sequencing, and instructions to indicate an event condition on the graph if the data quality falls below a predefined threshold.

Various embodiments of the run-time monitoring system can include a computer system and/or processor configured to determine various amounts and/or types of sequencing information or information relating to a sample and such information can be displayed in various manners. The next few FIGS. provide various examples of typical instrument runs and manners and types of information which can be determined and presented to a user by the system via some type of user interface (e.g., a GUI). These FIGS. are in no way meant to limit the type of information determined and/or generated by the run-time monitoring system and are in no way meant to limit the manner in which such information is represented. These FIGS. are merely examples.

Figure 2:
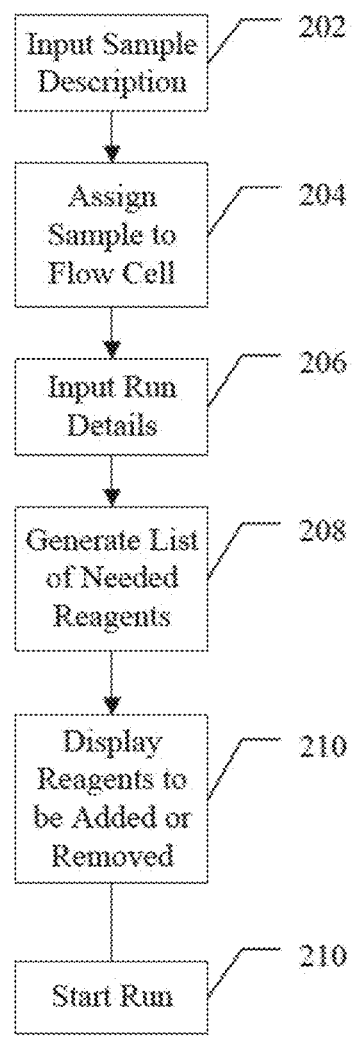
FIG. 2 is a flow diagram illustrating an exemplary embodiment of a method of starting a sequencing run.

By way of example, FIG. 2 provides a flowchart illustrating a run initiation sequence capable of being utilized with some embodiments of the present disclosure. At 202, a description of a sample to be sequenced is entered into the run-time system database via a user interface (e.g., a GUI). For example, the description can include a sample name, a sample description, library type, barcode information, and the like. At 204, the sample can be assigned to a sample processing unit. The sample can be assigned to a flowcell or a portion, such as a channel or lane, of the flow cell. At 206, run details can be entered. For example, a name for the run and a location for storing the results can be provided. Additionally, in some embodiments, a user can configure settings for notifications, reports, event handling, and exporting the results. In some embodiments, the user can provide a contact point, such as an email address or a mobile number for text messages. Additionally, in some embodiments, the user can select which types of events should cause a notification to be sent, such as when the run is complete, when the completion is delayed, when the system detects various events, and the like. Additionally, in some embodiments, the user may select to have reminders sent to the contact point, such as a reminder to replace reagents. In some embodiments, the user may select how events are handled, such as, for example, by pausing the run, by cancelling a single run in one channel while allowing runs of the remaining channels to continue, or automatically rerunning a primer. Further embodiments allow the user to select reports to be generated at if the results should be exported automatically upon completion or held for manual export. As would be apparent to the practitioner skilled in the art, other settings that control the function of the sequencing system during the sequencing run can also be configured by the user.

At 208, the sequencing system can generate a list of necessary reagents. The list of necessary reagents can be based on the type of library, a run length, or the like. For example, sequencing a mate-pair library can require different primers than sequencing a fragment library. Additionally, a longer run length can require more reagents, such as enzymes, nucleotides, probes, and the like, than a shorter run length. At 210, the sequencing system can display reagents that should be added or can be removed prior to the start of a sequencing run. For example, reagents that are not needed to perform the selected sequencing run can be removed from the instrument and stored. At 210, the run can be started.

Figure 3:
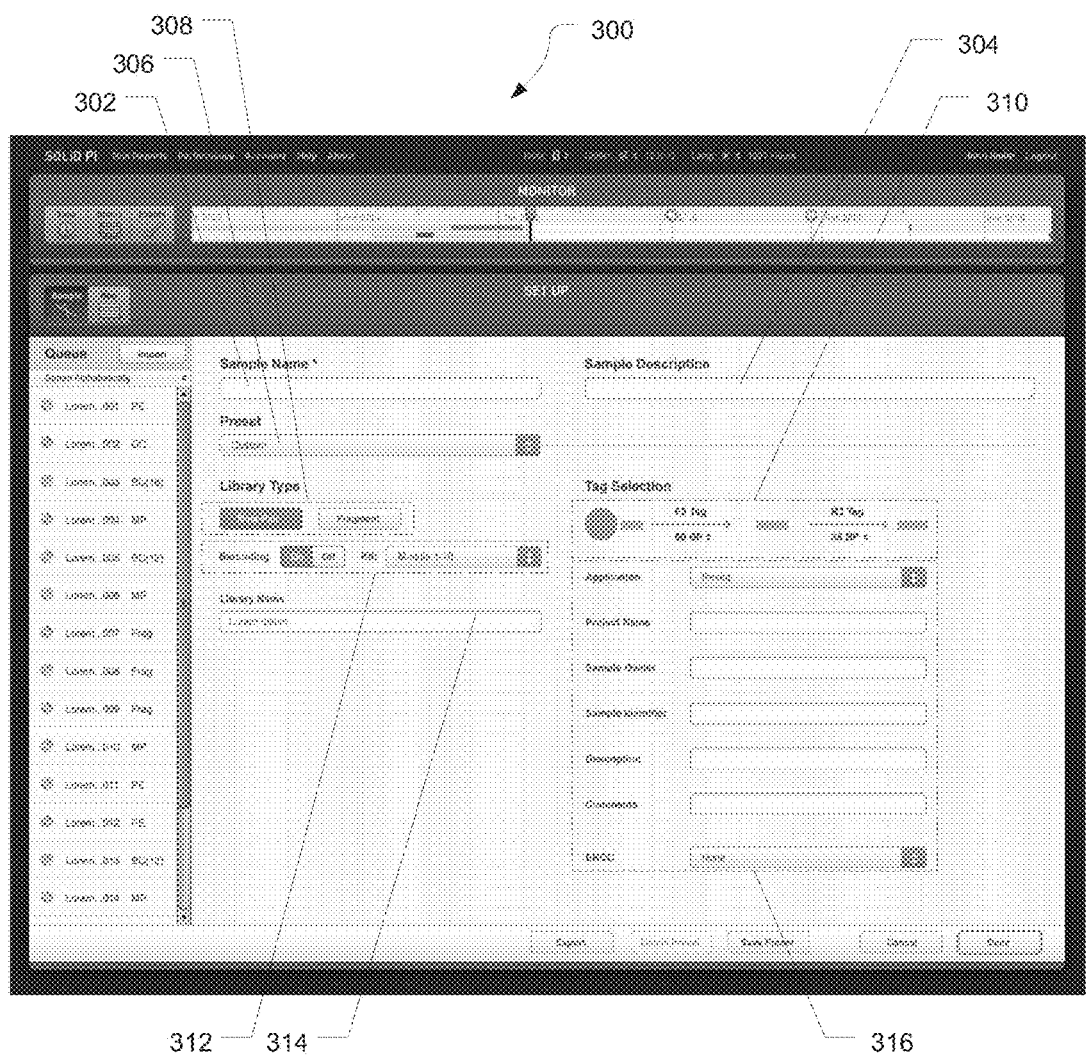
FIG. 3 is an illustration of an exemplary interface for entering information about a sample.

FIG. 3 provides an example of an interface 300 for entering the sample description into the run-time system. In some embodiments, the interface 300 can include an entry element 302 for supplying a sample name, and an entry element 304 for supplying a sample description. Entry elements 302 and 304 can include a text box, a text field, or the like. Additionally, in some embodiments, the interface 300 can include a selection element 306 to enable the user to select from a plurality of preset configurations. Selection element 306 can be a pull-down menu, or other interface element for selecting from a plurality of choices.

Further, in some embodiments, an interface 300 can include a selection element 308 for selecting a library type and a graphical representation 310 for displaying the primers to be used during the sequencing run and enabling the selection of the run length. In some embodiments, a selection element 308 can include buttons, radio buttons, or another element to enable the selection of one of limited number of predefined library types.

In some embodiments, the interface 300 can include a selection element 312 for enabling the multiplexing of bar coded samples. In some embodiments, multiple libraries can be generated, each having a short sequence of nucleic acids or bar code that has been added to distinguish the library from other libraries in the sample. By adding the different barcode to each of the libraries, multiple libraries can be combined in a single sample to be sequenced at the same time. Sequencing the barcode can enable each nucleic acid sequence to be associated with the corresponding library.

In some embodiments, the interface 300 can further include entry element 314 for entering a library name. Additional interface elements 316 can allow for additional information. In some embodiments, when barcoding is turned on, interface elements 314 and 316 can be modified to enable the entry of multiple libraries. For example, a table may be presented for entering multiple library names and additional information for each of the libraries in the sample.

Figure 4:
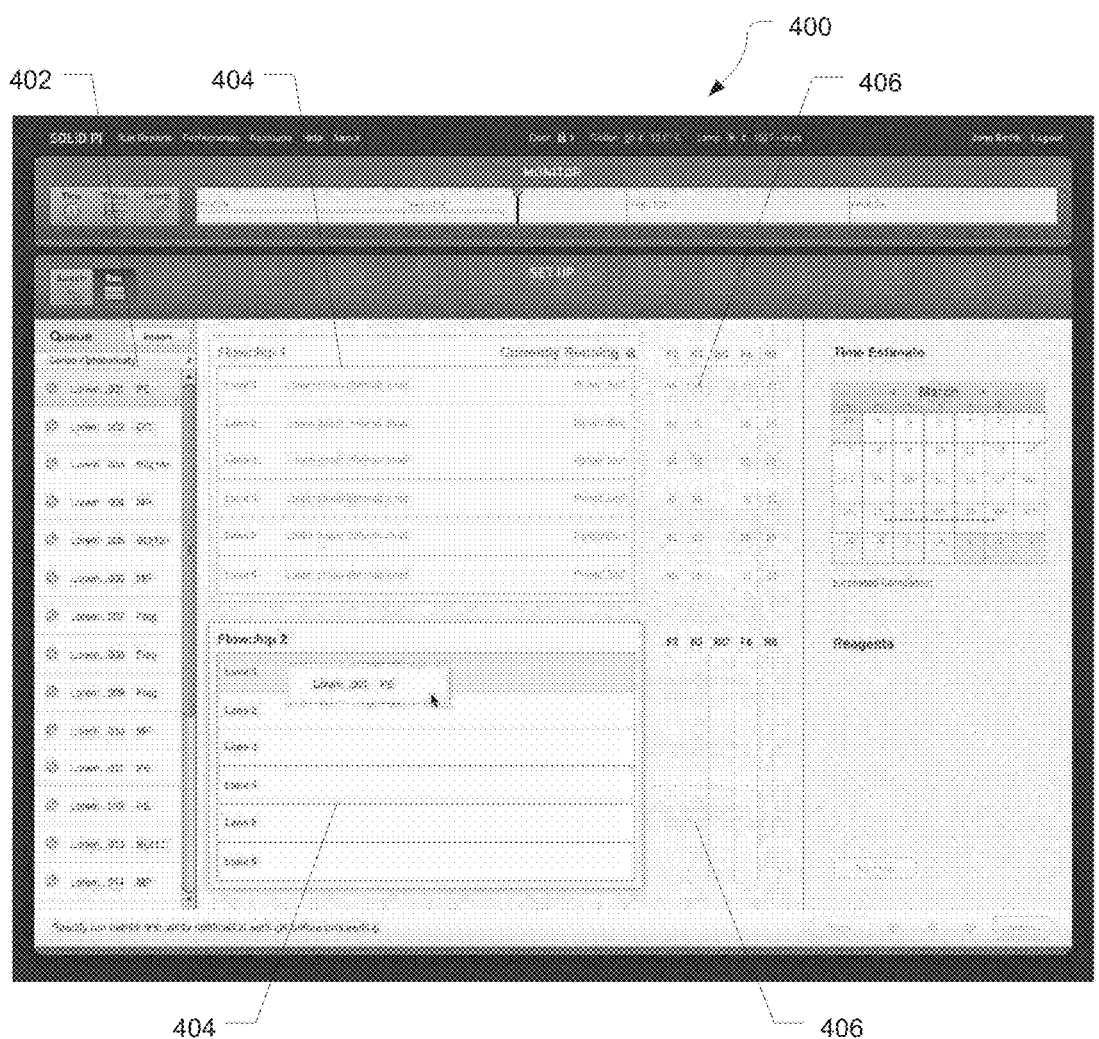
FIG. 4 is an illustration of an exemplary interface for assigning samples to a sample processing unit.

FIG. 4 illustrates an example of an interface 400 for assigning a sample to a flow cell in accordance with some embodiments. In some embodiments, the interface 400 can include a list 402 of samples and a representation 404 of the sample processing unit. In some embodiments, when two or more sample chambers are available, such as in a sequencing system with two flowcells, and one of the sample chambers or channels is currently performing a sequencing run, the representation 404 for the currently running sample chamber can be grayed out to indicate changes should not be made to the sample chamber while a sequencing run is in process. However, samples can be assigned to a sample chamber not currently engaged in a sequencing run. In some embodiments, the sample can be dragged from a sample queue to the sample chamber or a portion thereof, such as a channel or lane of a flow cell. Additionally, interface 400 may include a representation 406 of the sequencing process to be performed on the sample. The representation 406 can indicate the primers to be used and the run length associated with each primer.

Figure 5:
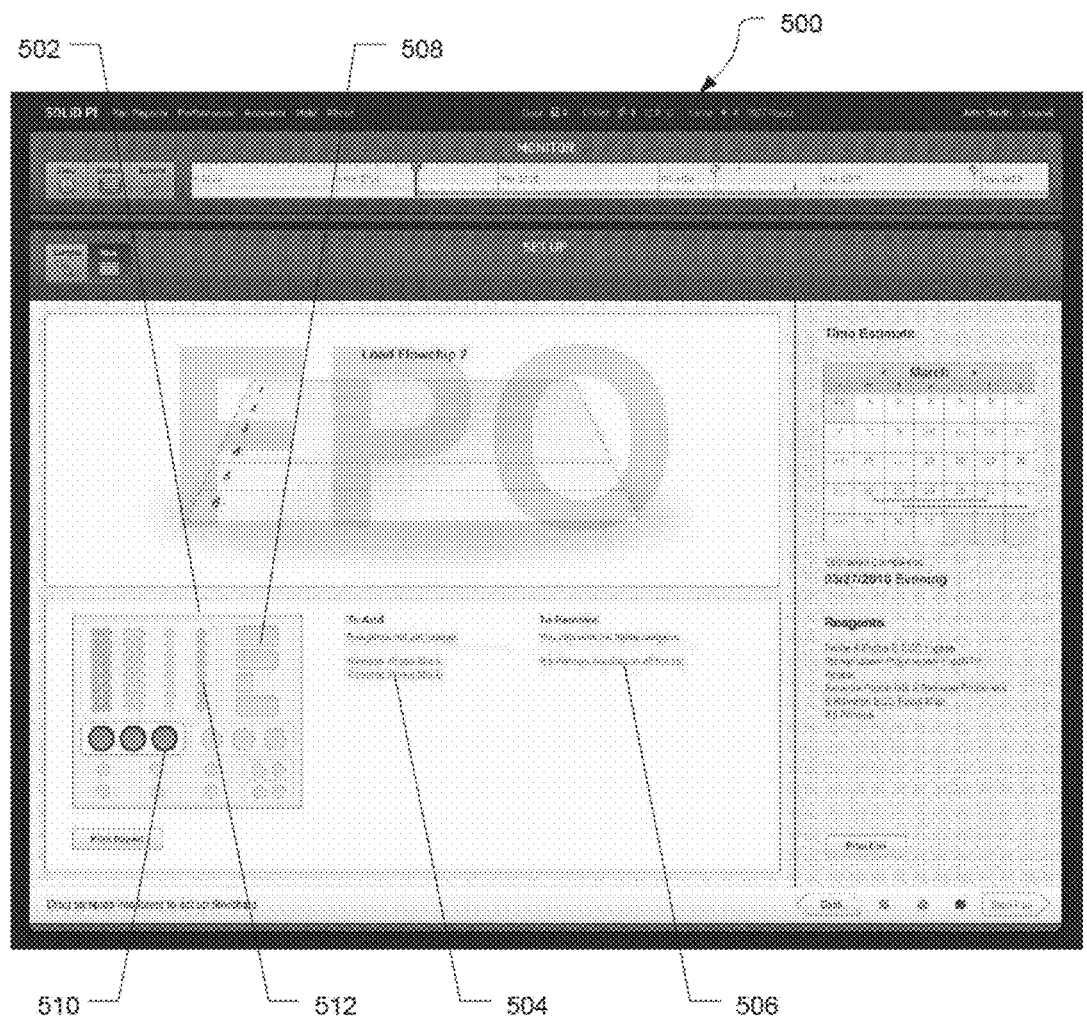
FIGS. 5 and 6 are illustrations of exemplary interfaces for displaying reagent information.

FIG. 5 illustrates an example of an interface 500 for displaying reagent information in accordance with some embodiments. In some embodiments, the interface 500 can include a representation 502 of the reagent storage area, a list 504 of reagents to be added, and a list 506 of reagents that can be removed. In some embodiments, the representation 502 can be coded (e.g., color coded) to indicate where the reagents to be added or removed should be located. For example, in some embodiments, regions 508 of the reagent storage area that correspond to needed reagents that are present or unneeded reagents that are not present can be colored green, regions that correspond to needed reagents that are not present can be colored red, and regions corresponding to unneeded reagents that can be removed can be colored yellow. Additionally, in some embodiments, the lists 504 and 506 may also be colored to match the representation 502.

Figure 6:
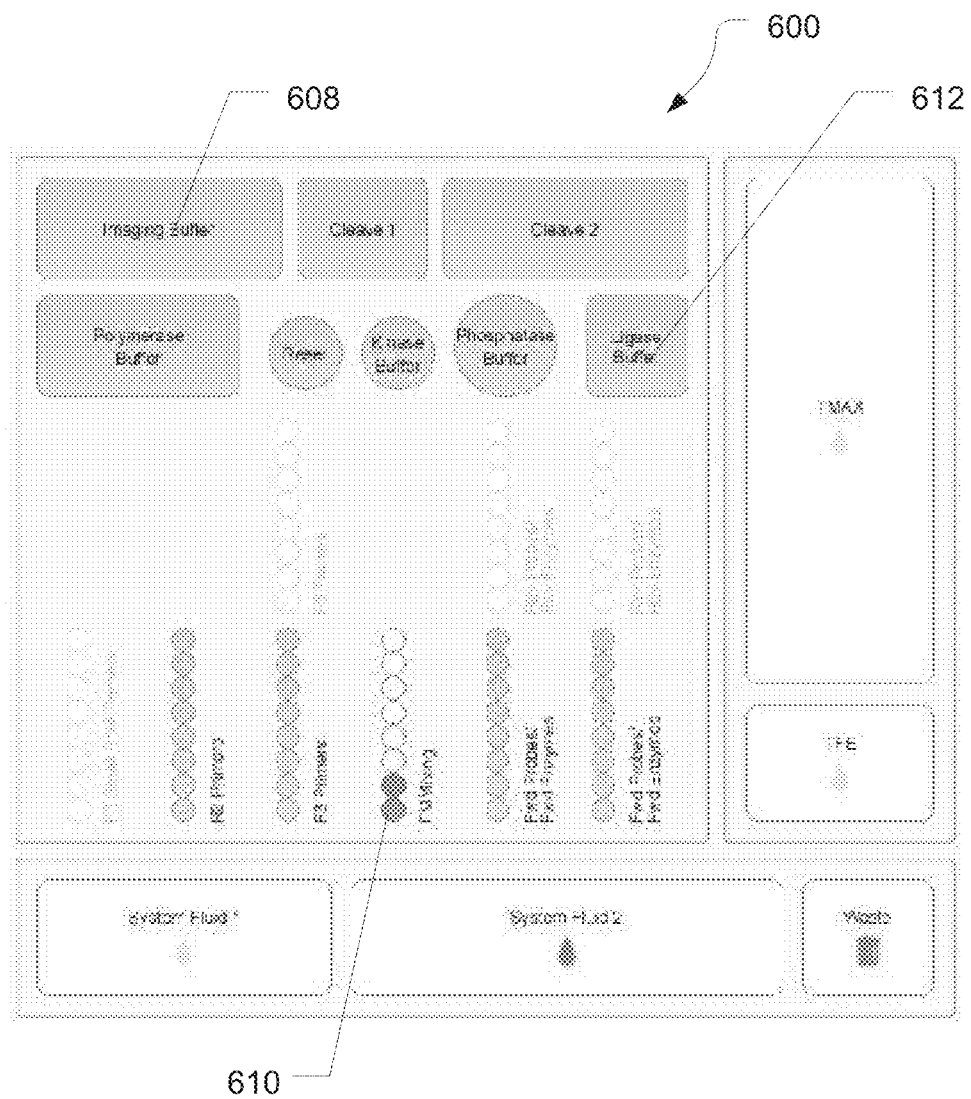

FIG. 6 illustrates another example of a representation 602 of the reagent storage area capable of being used with some embodiments. Regions 614 colored blue may indicate needed reagents that are present but may need to be changed or replaced during the sequencing run.

Figure 7:
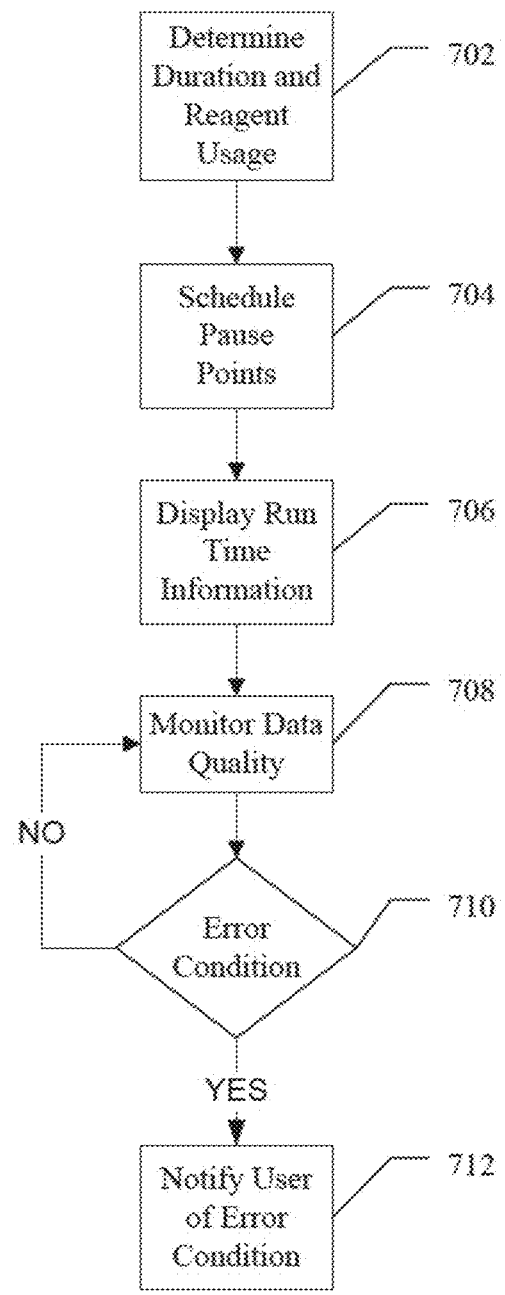
FIG. 7 is a flow diagram illustrating an exemplary embodiment of a method for monitoring a sequencing run.

In some embodiments, FIG. 7 illustrates an exemplary method for monitoring a sequencing run. For example, at 702, a sequencing system can determine the duration of the sequencing run. Additionally, in some embodiments, the system can determine the amount of reagents available and the amount of the reagents needed to complete the sequencing run. When the amount of reagents available does not exceed the amount of the reagents needed to complete the sequencing run, the system can schedule a pause point, as illustrated at 704, to pause the sequencing run and wait for additional reagents to be added. For example, in some embodiments, if the system determines that an amount of available enzyme is not sufficient to complete the sequencing run, the system can determine the point at which the amount of available enzyme will run out, and schedule a pause point to pause the sequencing run at a point prior to when the available enzyme will run out, so that additional enzyme can be added.

At 706, the system can display run time information for the sequencing run, such as when the run will be completed and the times of any scheduled pause points. The run time information can be displayed in various forms, including in a timeline, on a calendar, in a list of events, or the like. For example, a timeline spanning several days can be divided into hours. A bar representing the duration of the run can be overlaid along the timeline, and scheduled pause points can be indicated at the appropriate location along the timeline. In some embodiments, a calendar may display the length of a sequencing run spanning several days, or a list of events may include a data, time, and description of each event, such as a pause point or a beginning or end of a sequencing run.

Figure 8:
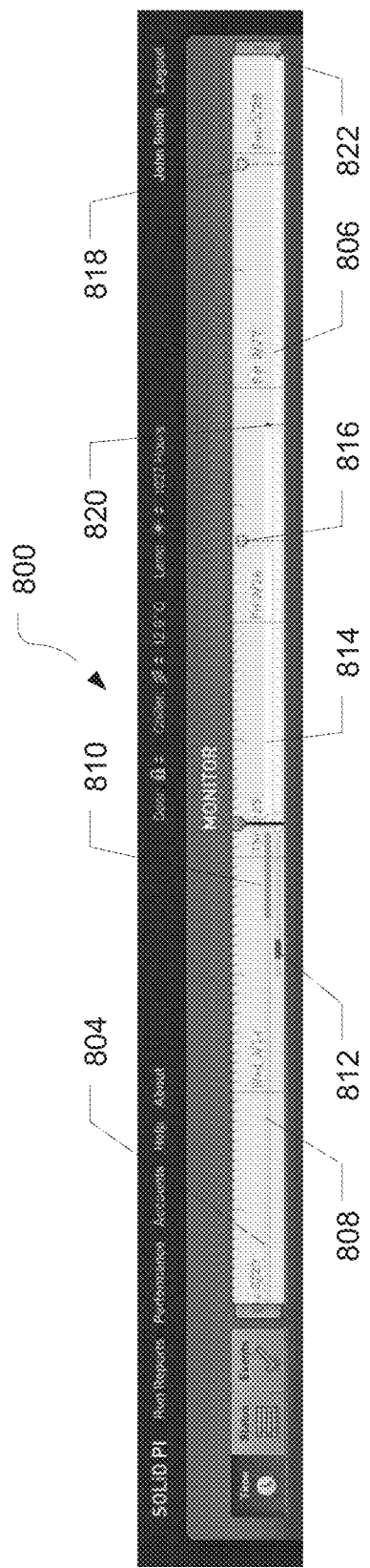
FIGS. 8 and 9 are illustrations of exemplary interfaces for displaying run time information.

FIG. 8 illustrates a representation of a timeline 800 in accordance with some embodiments of the presently disclosed system capable of graphically showing run time information for a sequencing run. In some embodiments, the timeline 800 can show duration bars 804 and 806 showing the duration of ongoing sequencing runs. In some embodiments, the duration bars 804 and 806 can be divided into colored portions to further indicate events during and progress through the sequencing run. For example, in some embodiments, a green portion 808 can indicate or represent a portion of the sequencing run that has been completed without events, an orange portion 810 can indicate or represent a time period when the sequencing run was paused waiting for user input or additional reagents, a red portion 812 can indicate or represent a time period when an event condition was detected, and a white portion 814 can indicate or represent a portion of the sequencing run that has not yet occurred. In some embodiments, the timeline 800 can indicate scheduled pause points 816 and 818, and end points 820 and 822. In some embodiments, the pause points can be times when the sequencing run will be paused to wait for additional reagents or other user input.

Figure 9:
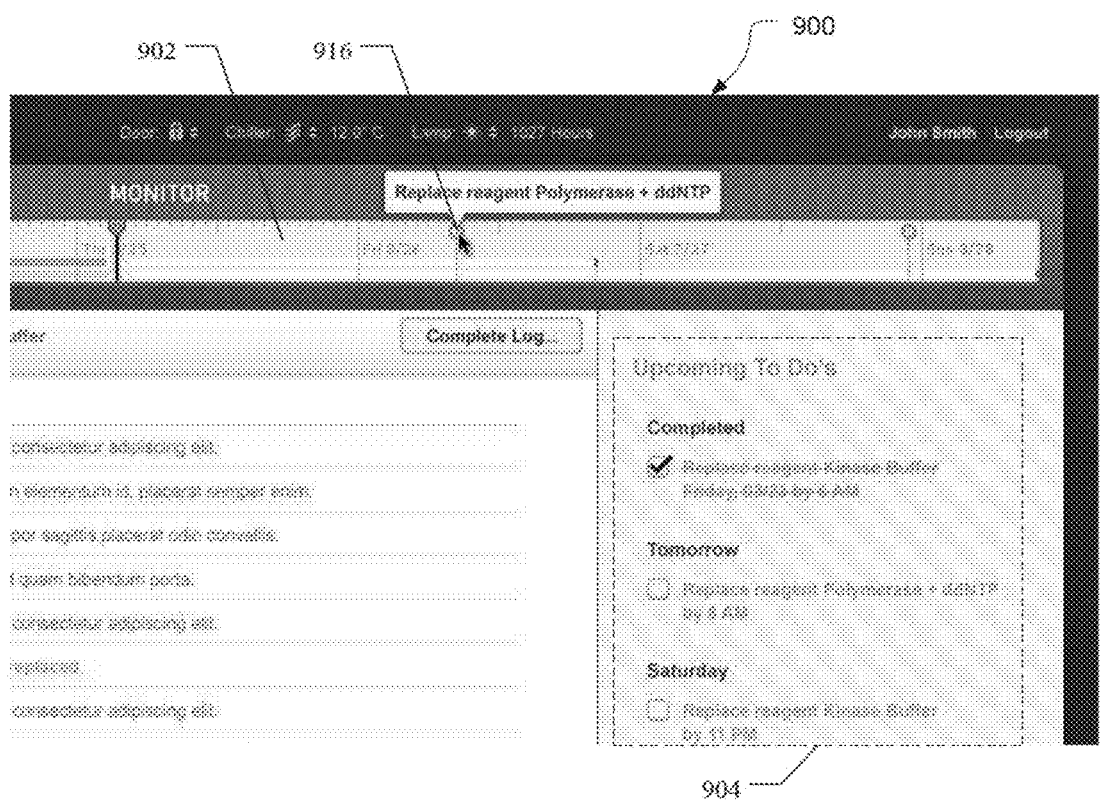

FIG. 9 illustrates an example of an interface 900 for supplying run time information capable of being used in accordance with some embodiments of the presently disclosed system. For example, an interface 900 can include a timeline 902 similar to timeline 800. In some embodiments, interface 900 can include a list 904 of upcoming items corresponding to scheduled pause points. In some embodiments, the list 904 can indicate a description of the activity in addition to the date and time of the activity. In some embodiments, a description of the activity can be displayed when a cursor moves over a pause point 916 indicated on the timeline 902.

Returning to FIG. 7, in some embodiments, the sequencing system can monitor the data quality during the run, as illustrated at 708, and at 710, the system can determine if there is an event condition. In some embodiments, when there is an event condition, the sequencing system can notify the user of the event condition, as illustrated at 712. In some embodiments, when there is not an event condition, the system can return to 708 to continue to monitor the data quality. In some embodiments, the sequencing system may pause or abort a sequencing run or a portion of the sequencing run in response to the event condition. In some embodiments, the system can be configured to automatically take some corrective action in response to some event condition.

In some embodiments, during the run the sequencing system can monitor quality of the data for a control set and the quality of data for a nucleic acid sample. When the quality of the data for the nucleic acid sample falls below a predetermine threshold but the quality of the data for the control set remains above the predetermined threshold, there may have been a problem with the sample preparation. In some embodiments, when the quality of the data for the nucleic acid sample and the quality of the data for the control set both fall below the predetermined threshold, there may be a problem with the sequencing run. In some embodiments, the sequencing system may perform different event handling operations depending on the source of the error.

Figure 10:
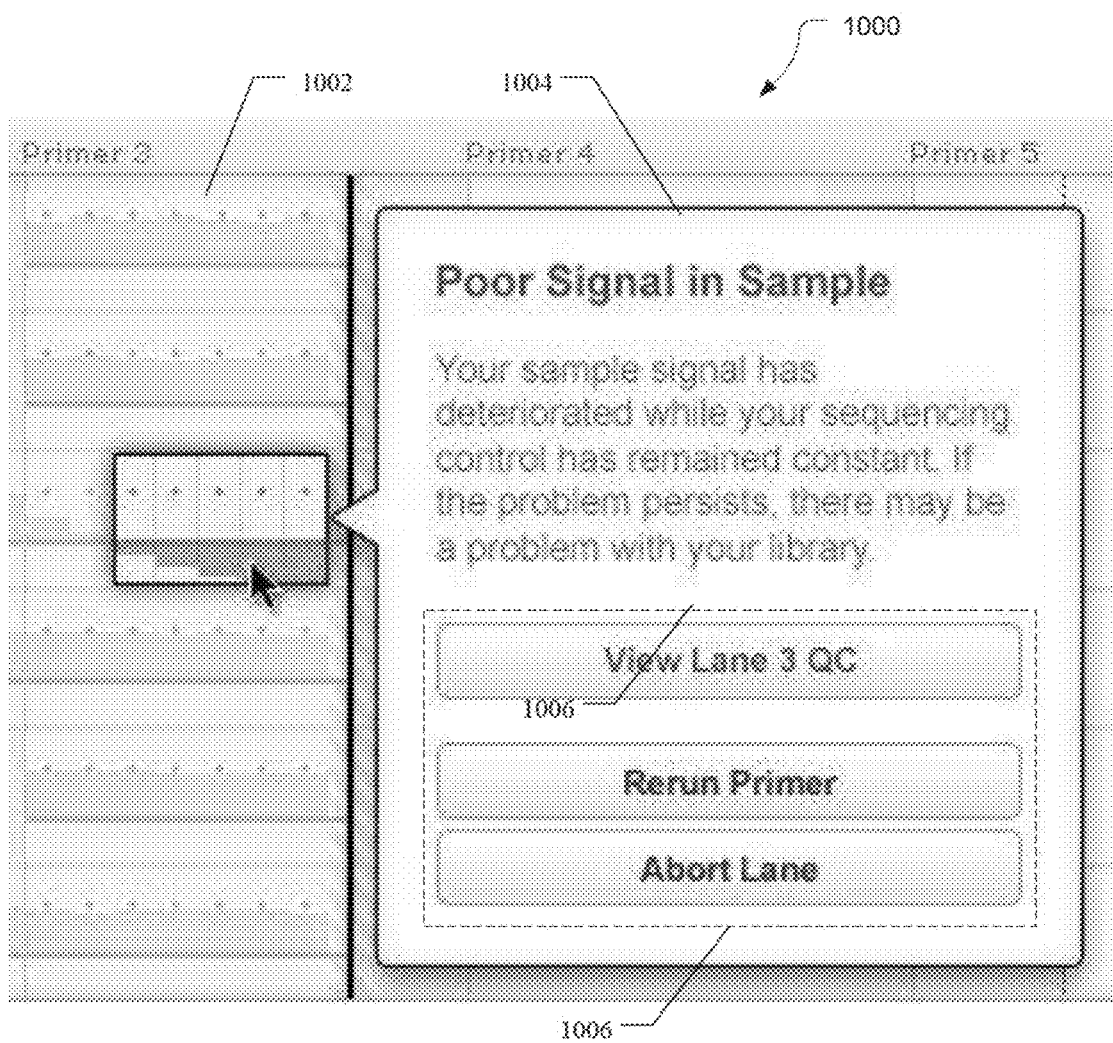
FIG. 10 is an illustration of an exemplary interface for displaying information about the data quality.

In accordance with some embodiments, FIG. 10 provides an example of a notification interface 1000. In some embodiments, the notification interface can include a display 1002 of signal quality during each portion of the sequencing run. The signal quality can be graphically illustrated relative to the predefined threshold. In some embodiments, the display 1002 can be color coded, such that portions of the sequencing run where the signal quality is above the threshold are distinguished from portions of the sequencing run where the signal quality is below the threshold. In some embodiments, the notification interface 1000 can include an explanation of the event condition 1004 and a set of actions 1006. In some embodiments, the explanation of the event condition 1004 can provide the user with a description of an error and a probable source of the error, such as based on a comparison of the control data to the sample data. The set of actions 1006 can enable the user to abort the sequencing run of a nucleic acid sample or to repeat a portion of the sequencing run. Other actions will be apparent to the practitioner skilled in the art.

Figure 11:
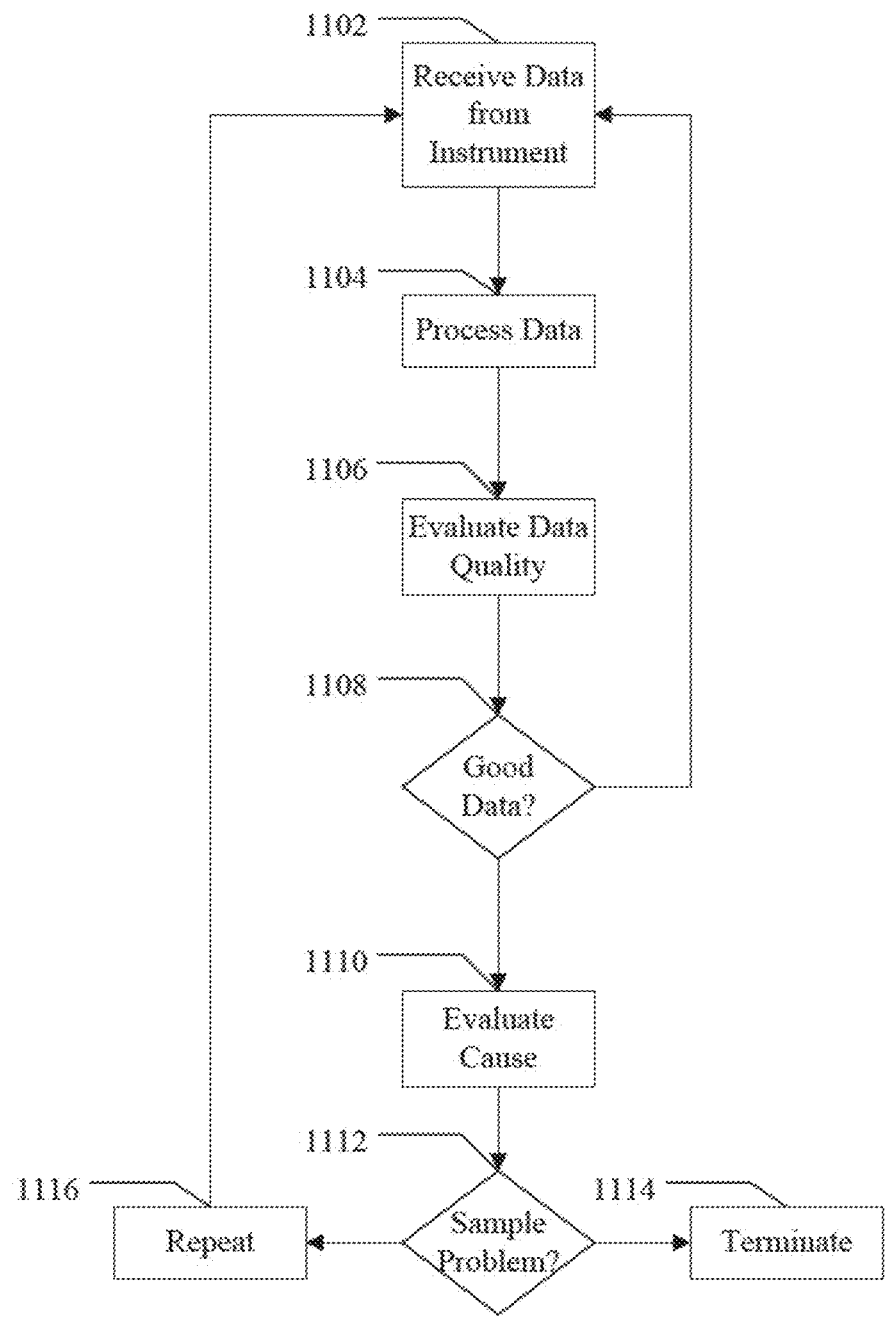
FIG. 11 is a flow diagram illustrating another exemplary embodiment of a method for monitoring a sequencing run.

In some embodiments, FIG. 11 illustrates an exemplary method for monitoring an instrument run. For example, at 1102, a processor can receive data from an instrument, such as a sequencing instrument. The data can include information relating to a signal, such as a fluorescent signal, a luminescent signal, a chemiluminescent signal, a measured current, voltage or resistance, a measured proton or ion concentration or generation, or the like. Additionally, the data can include information relating to a control, a sample, or a combination thereof.

At 1104, the processor can process the data. For example, the processor can utilize the data to determine a call, such as a color call, a base call, or a nucleotide call for a sample or a control. In particular embodiments, processing the data can require a number of processing steps, such as for example, aligning multiple images, identify sample and control locations, evaluating multiple signal intensities for each location, and the like.

At 1106, the processor can evaluate the data quality. For example, the processor can determine a quality value for the call. Additionally, the processor can compare the quality value to an expected quality value. In particular embodiments, prior sequencing runs can be used to determine the expected quality value.

At 1108, the processor can determine if the data is good, such as sufficient for determining the sequencing of the sample. For example, the processor can determine the data is good when the quality value is within a predetermined range of the expected quality value. When the data is good, the processor can receive additional data from the instrument at 1102.

Alternatively, when the data quality is not good, the processor can evaluate the cause of the problem, as illustrated at 1110. For example, the processor can compare the data quality of the sample to the data quality of the control to determine if the problem is with the sample or with the sequencing run, such as with the instrument, the reagents, or the like. At 1112, the processor can determine if the problem is with the sample, and when the problem is with the sample, the processor can instruct the sequencing instrument to terminate a portion of the sequencing run, as illustrated at 1114. Alternatively, when the problem is not with the sample, the processor can instruct the sequencing instrument to repeat a portion of the sequencing run, as illustrated at 1116.

Significantly, processing and evaluating of the data can occur after image or data collection and prior to any additional steps of the sequencing run. This can enable the processor to identify problems with the current step of sequencing run, evaluate the cause of the problem, and determine corrective action prior to additional steps being performed. In this way, portions of the sequencing run may be salvaged and reagents and instrument time may be conserved.

In various embodiments, the processor can determine a distribution of quality values for a set of controls and determine a distribution of quality values for a set of samples. The quality value distributions can be compared to an expected quality value distribution. For example, the expected distribution determined from controls in prior sequencing runs on the sequencing instrument. Further each of the sample quality value distribution and the control quality value distribution can be scored relative to the expected quality value distribution. Scores for the sample quality value distribution or the control quality value distribution that fall outside a predetermined range can indicate a problem with the sequencing run. Further, comparing the scores for the sample and control can provide an indication of the source of the problem. In particular embodiments, the processor can instruct the sequencing instrument to modify the run based on the comparison of the scores. For example, when the score of the sample is outside the predetermined range and the score of the control is within the predetermined range, the source of the problem may be with the sample preparation and the processor can instruct the sequencing instrument to terminate a portion of the sequencing run, such as a lane indicating the problem or subsequent ligation cycles. Alternatively, when scores for both the sample and control are outside of the predetermined range, the source of the problem may be with the sequencing run, and the processor can instruct the sequencing instrument to repeat a portion of the sequencing run.

Figure 12:
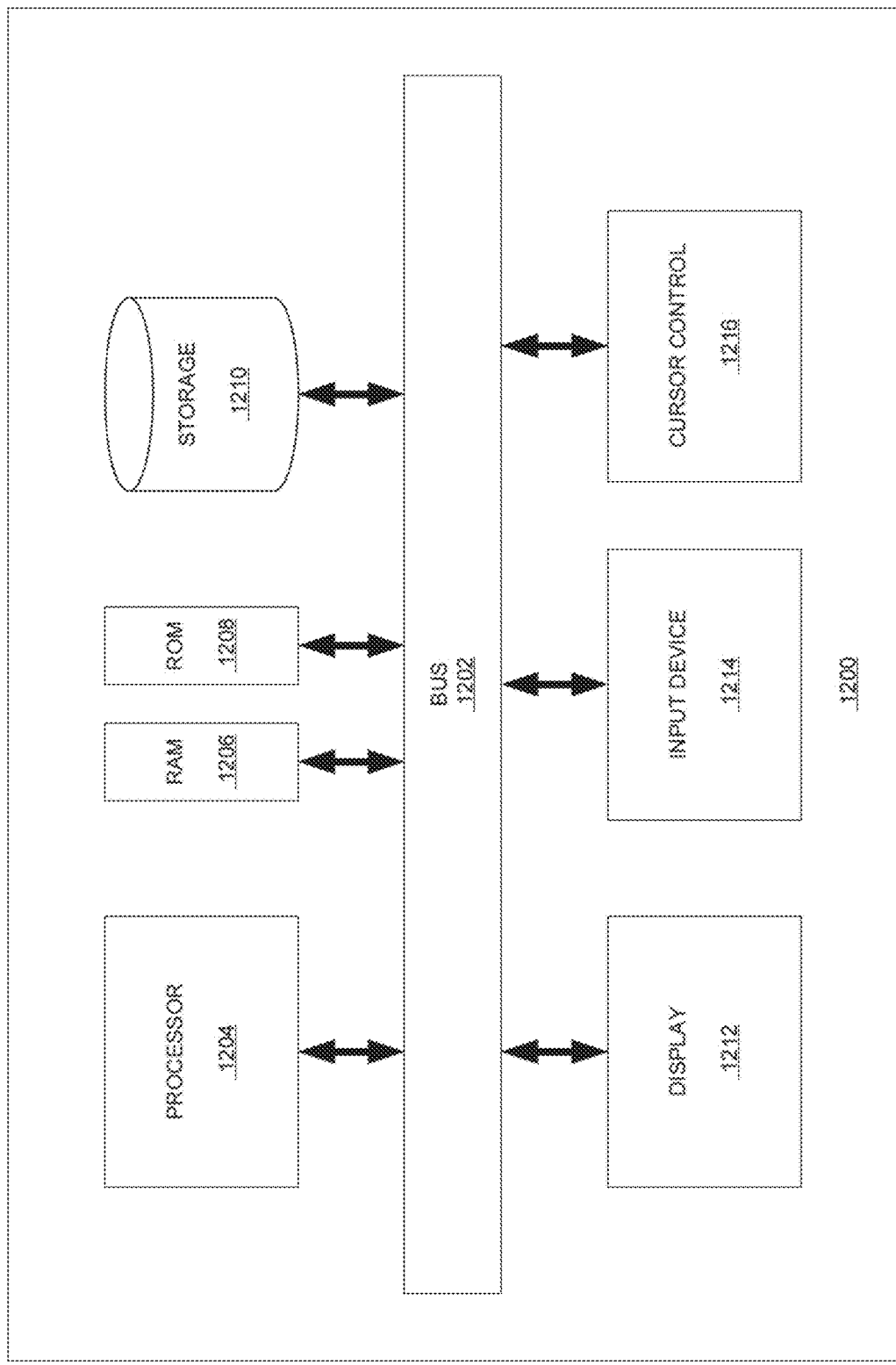
FIG. 12 is a block diagram illustrating an exemplary computer system.

FIG. 12 is a block diagram that illustrates a computer system 1200, upon which embodiments of the present teachings can be implemented. Examples of a computer system 1200 can include a server system or client system, such as desktop or laptop, or a mobile or handheld system, such as a PDA, smartphone, tablet, or the like. Computer system 1200 can be a general purpose computer, such as a general-purpose computer program performs specific functions, or a special-purpose computer.

Computer system 1200 can include a bus 1202 or other communication mechanism for communicating information, and a processor 1204 coupled with bus 1202 for processing information. In various embodiments, the processor 1204 can include a Central Processing Unit (CPU), such as a coreDuo, a Nehalem, an Athlon, an Opteron, a PowerPC, or the like, a Graphics processing unit (GPU), such as the GeForce, Tesla, Radeon HD, or the like, an Application-specific integrated circuit (ASIC), a Field programmable gate array (FPGA), or the like. In various embodiments, the processor 1204 can include a single core processor or a multi-core processor. Additionally, multiple processors can be coupled together to perform tasks in parallel.

Computer system 1200 can also include a memory 1206, which can be a random access memory (RAM) or other dynamic storage device, coupled to bus 1202. Memory 1206 can store data, such as sequence information, and instructions to be executed by processor 1204. Memory 1206 can also be used for storing temporary variables or other intermediate information during execution of instructions to be executed by processor 1204. Computer system 1200 can further include a read-only memory (ROM) 1208 or other static storage device coupled to bus 1202 for storing static information and instructions for processor 1204. A storage device 1210, such as a magnetic disk, an optical disk, a flash memory, or the like, can be provided and coupled to bus 1202 for storing information and instructions.

Computer system 1200 can be coupled by bus 1202 to display 1212, such as a cathode ray tube (CRT) or liquid crystal display (LCD), for displaying information to a computer user. An input device 1214, such as a keyboard including alphanumeric and other keys, can be coupled to bus 1202 for communicating information and commands to processor 1204. Cursor control 1216, such as a mouse, a trackball, a trackpad, or the like, can communicate direction information and command selections to processor 1204, such as for controlling cursor movement on display 1212. The input device can have at least two degrees of freedom in at least two axes that allows the device to specify positions in a plane. Other embodiments can include at least three degrees of freedom in at least three axes to allow the device to specify positions in a space. In additional embodiments, functions of input device 1214 and cursor 1216 can be provided by a single input devices such as a touch sensitive surface or touch screen.

Computer system 1200 can perform the present teachings. Consistent with certain implementations of the present teachings, results are provided by computer system 1200 in response processor 1204 executing one or more sequences of one or more instructions contained in memory 1206. Such instructions may be read into memory 1206 from another computer-readable medium, such as storage device 1210. Execution of the sequences of instructions contained in memory 1206 can cause processor 1204 to perform the processes described herein. Alternatively, hard-wired circuitry may be used in place of or in combination with software instructions to implement the present teachings. Thus, implementations of the present teachings are not limited to any specific combination of hardware circuitry and software.

The term "computer-readable medium" as used herein refers to any media that participates in providing instructions to processor 1204 for execution. Such a medium may take many forms, including but not limited to, nonvolatile memory, volatile memory, and transmission media. Non-volatile memory includes, for example, optical or magnetic disks, such as storage device 1210. Volatile memory includes dynamic memory, such as memory 1206. Transmission media includes coaxial cables, copper wire, and fiber optics, including the wires that comprise bus 1202. Non-transitory computer readable medium can include non-volatile media and volatile media.

Common forms of non-transitory computer readable media include, for example, floppy disk, flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, and other memory chips or cartridge or any other tangible medium from which the computer can read.

Various forms of computer readable media may be involved in carrying one or more sequences of one or more instructions to processor 1204 for execution. For example the instructions may initially be stored on the magnetic disk of a remote computer. The remote computer can load the instructions into its dynamic memory and send instructions over a network to computer system 1200. A network interface coupled to bus 1202 can receive the instructions and place the instructions on bus 1202. Bus 1202 can carry the instructions to memory 1206, from which processor 1204 can retrieve and execute the instructions. Instructions received by memory 1206 may optionally be stored on storage device 1210 either before or after execution by processor 1204.

In a first aspect, a system for sequencing nucleic acid samples can include a sequencing instrument and a processor in communication with the sequencing instrument. The sequencing instrument can be configured to interrogate a control set and a nucleic acid sample to produce control data for the control set and sample data for the nucleic acid sample. The processor can be configured to receive the control data and the sample data from the sequencing instrument; compare the control data to the sample data; and perform an event handling routines based on the comparison of the control data to the sample data.

In various embodiments, the processor can be further configured to determine a control quality value for the control data and a sample quality value for the sample data. In particular embodiments, the processor can be further configured to generate a graphical representation of the sample quality value.

In various embodiments, the event handling routine can include providing an event notification, instructing the sequencing instrument to suspend interrogating the nucleic acid sample, generating a log entry, or any combination thereof. In particular embodiments, providing an event notification can include sending an electronic message, displaying an alert, or any combination thereof. In particular embodiments, providing an event notification can include providing an explanation of the probable cause of the event condition based on comparing the control quality value, the sample quality value, and the threshold.

In various embodiments, the processor can be further configured to determine a required amount of a reagent needed by a sequencing instrument to sequence a nucleic acid sample, and determine an available amount of the reagent. The processor can further be configured to identify a time when the sequencing instrument will need an additional amount of the reagent if the required amount exceeds the available amount, and notify an operator of the time when the sequencing instrument will need an additional amount of the reagent. Additionally, the processor can be configured to instruct the sequencing instrument to suspend interrogating the nucleic acid sample prior to the time when the sequencing instrument will need the additional amount of the reagent, and instruct the sequencing instrument to resume interrogating the nucleic acid sample when the additional amount of the reagent has been added.

In a second aspect, a computer-implemented method can include receiving control data and sample data from a sequencing instrument, determining a control quality value for the control data and a sample quality value for the sample data; comparing the control quality value for the control data to an expected control quality value; and the sample quality value for the sample data to an expected sample quality value; and determining an event condition based on the comparison.

In various embodiments, the method can further include displaying a graphical representation of the sample quality value.

In various embodiments, the method can further include performing an event handling routine based on the event condition. The event handling routine can include providing an event notification, instructing the sequencing instrument to suspend interrogating the nucleic acid sample, generating a log entry, or any combination thereof. In particular embodiments, providing an event notification can include sending an electronic message, displaying an alert, or any combination thereof. In particular embodiments, providing an event notification can include providing an explanation of the probable cause of the event condition based on comparing the control quality value, the sample quality value, and the threshold.

In various embodiments, the method can further include determining a required amount of a reagent needed by a sequencing instrument to sequence a nucleic acid sample, and determining an available amount of the reagent. The method can further include identifying a time when the sequencing instrument will need an additional amount of the reagent if the required amount exceeds the available amount, and notifying an operator of the time when the sequencing instrument will need an additional amount of the reagent. Additionally, the method can include instructing the sequencing instrument to suspend interrogating the nucleic acid sample prior to the time when the sequencing instrument will need the additional amount of the reagent, and instructing the sequencing instrument to resume interrogating the nucleic acid sample when the additional amount of the reagent has been added.

In a third aspect, a computer program product can include a non-transitory computer-readable storage medium whose contents include a program with instructions to be executed on a processor. The instructions can include instructions to obtain control data and sample data from a sequencing instrument; instructions to determine a control quality value for the control data and a sample quality value for the sample data; instructions to compare the control quality value and the sample quality value; and instructions to perform an event handling routine when the control quality value or the sample quality value is below a threshold.

In various embodiments, the computer program product can further include instructions to generate a graphical representation of the sample quality value.

In various embodiments, instructions to perform the event handling routine can include instructions to provide an event notification, instruction to notify the sequencing instrument to suspend interrogating the nucleic acid sample, instructions to generate a log entry, or any combination thereof. In particular embodiments, the instructions to provide an event notification can include instructions to send an electronic message, instructions to display an alert, or any combination thereof. In particular embodiments, the instructions to provide an event notification can include instructions to provide an explanation of the probable cause of the event condition based on comparing the control quality value, the sample quality value, and the threshold.

In various embodiments, the computer program product can further include instructions to determine a required amount of a reagent needed by a sequencing instrument to sequence a nucleic acid sample; instructions to determine an available amount of the reagent; instructions to identify a time when the sequencing instrument will need an additional amount of the reagent if the required amount exceeds the available amount; instructions to notify an operator of the time when the sequencing instrument will need an additional amount of the reagent; instructions to notify the sequencing instrument to suspend interrogating the nucleic acid sample prior to the time when the sequencing instrument will need the additional amount of the reagent; and instructions to notify the sequencing instrument to resume interrogating the nucleic acid sample when the additional amount of the reagent has been added.

In a forth aspect, a computer program product can include a non-transitory computer-readable storage medium whose contents include a program with instructions to be executed on a processor. The instructions can include instructions to determine a duration for sequencing a nucleic acid sample by a sequencing instrument; instructions to display a graph indicating the duration; instructions to monitor the process of the sequencing and display the progress on the graph; instructions to determine a data quality for the sequencing; and instructions to indicate an event condition on the timeline if the data quality falls below a predefined threshold.

In various embodiments, the computer program product can include instructions to determine a required amount of a reagent needed by a sequencing instrument to sequence a nucleic acid sample; instructions to determine an available amount of the reagent; instructions to identify a time when the sequencing instrument will need an additional amount of the reagent if the required amount exceeds the available amount; instructions to schedule an event prior to the time, the event including instructing the sequencing instrument to stop sequencing the nucleic acid, notifying an operator to add an additional amount of the reagent, and instructing the sequencing instrument to continue sequencing after the additional amount is added.

In particular embodiments, the computer program product can further include instructions to indicate the event on the graph. In particular embodiments, the computer program product can further include instructions to display a representation of a reagent storage area of the sequencing instrument to indicate where the additional amount of the reagent should be added.

In a fifth aspect, a computer-implemented method can include receiving data from a sequencing instrument performing a sequencing run; processing the data to determine a fist call for a sample; calculating a first quality value for the first call; and evaluating a run quality of the sequencing run based on the first quality value.

In various embodiments, the call can be a color call, a base call, or a nucleotide call. In various embodiments, evaluating the run quality can include comparing the first quality value to an expected quality value.

In various embodiments, the method can further include processing the data to determine a second call for a control; and calculating a second quality value for the second call, and wherein evaluating the run quality is further based on the second quality value. In particular embodiments, evaluating the run quality can include comparing the first quality value to a first expected quality value, and comparing the second quality value to a second expected value.

In particular embodiments, the method can further include sending an instruction to the sequencing instrument to repeat a portion of the sequencing run when comparing the first quality value to a first expected quality value and comparing the second quality value to a second expected value both indicate lower-than-expected run quality. In particular embodiments, the method can further include sending an instruction to the sequencing instrument to terminate a portion of the sequencing run when comparing the first quality value to a first expected quality value indicates lower-than-expected run quality, and comparing the second quality value to a second expected value does not indicates lower-than-expected run quality.

While the principles of the present teachings have been described in connection with specific embodiments of control systems and sequencing platforms, it should be understood clearly that these descriptions are made only by way of example and are not intended to limit the scope of the present teachings or claims. What has been disclosed herein has been provided for the purposes of illustration and description. It is not intended to be exhaustive or to limit what is disclosed to the precise forms described. Many modifications and variations will be apparent to the practitioner skilled in the art. What is disclosed was chosen and described in order to best explain the principles and practical application of the disclosed embodiments of the art described, thereby enabling others skilled in the art to understand the various embodiments and various modifications that are suited to the particular use contemplated. It is intended that the scope of what is disclosed be defined by the following claims and their equivalents.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Embodiments may include various processes. The processes may be performed by hardware components or may be embodied in machine-executable instructions, which may be used to cause a controller, a general-purpose or special-purpose processor, or logic circuits programmed with the instructions to perform the processes. Alternatively, the processes may be performed by a combination of hardware and software. Further, embodiments may be implemented on stand-alone computing devices, a cluster of computing devices, a cloud or distributed network of computing devices, portable computing devices, mobile computing devices, or wireless computing devices.

Certain embodiments can also be implemented in code and may be stored on a computer readable medium having stored thereon instructions which can be used to program a computer system to perform the instructions. The computer readable medium may be any data storage device that can store data, which can thereafter be read by a computer system. Examples of the computer readable medium may include, but is not limited to, any type of disk including magnetic tapes, floppy disks, hard drives, network attached storage (NAS), optical disks, compact disk read-only memories (CD-ROMs), compact disk writeable (CD-Rs), compact disk rewriteable (CD-RWs), and magneto-optical disks, semiconductor devices such as read-only memories (ROMs), random access memories (RAMs), erasable programmable read-only memories (EPROMs), flash memories, electrically erasable programmable read-only memories (EEPROMs), magnetic optical cards, or any type of media suitable for storing electronic instructions. The computer readable medium can also be distributed over a network coupled computer systems so that the computer readable code is stored and executed in a distributed fashion.

What is claimed is:

1. A system for sequencing nucleic acid samples, the system comprising:
   a sequencing instrument for interrogating a control set comprising a collection of differing nucleic acids each having a known sequence and known physical properties and a nucleic acid sample for producing control data for the control set and sample data for the nucleic acid sample; and
   a processor in communication with the sequencing instrument configured to:
      receive the control data and the sample data from the sequencing instrument;
      compare an intensity, a relative intensity, or a quality of the control data to an intensity, a relative intensity, or a quality of the sample data;
      perform an event handling routine based on the comparison of the intensity, relative intensity, or quality of the control data to the intensity, relative intensity, or quality of the sample data;
      determine a required amount of a reagent needed by a sequencing instrument to sequence the nucleic acid sample;
      determine an available amount of the reagent;
      identify a time at which the sequencing instrument will need an additional amount of the reagent in response to determining that the required amount exceeds the available amount;
      notify an operator of the time at which the sequencing instrument will need an additional amount of the reagent;
      instruct the sequencing instrument to suspend interrogating the nucleic acid sample prior to the time at which the sequencing instrument will need the additional amount of the reagent; and
      instruct the sequencing instrument to resume interrogating the nucleic acid sample in response to determining that the additional amount of the reagent has been added.

2. The system of claim 1, wherein the processor is further configured to determine a control quality value for the control data and a sample quality value for the sample data.

3. The system of claim 2, wherein the processor is further configured to generate a graphical representation of the sample quality value.

4. The system of claim 2, wherein the event handling routine includes providing an event notification.

5. The system of claim 4, wherein providing an event notification includes sending an electronic message.

6. The system of claim 4, wherein providing an event notification includes providing an explanation of the probable cause of an event condition based on comparing the control quality value, the sample quality value, and a threshold.

7. The system of claim 1, wherein the control set comprises a set of solid supports each having a collection of nucleic acids of known sequence and physical properties attached thereto.

8. The system of claim 1, wherein the control set comprises a solid support having a collection of nucleic acids of known sequence and physical properties attached thereto such that each of the nucleic acids is located at a substantially distinct location on the solid support.

9. The system of claim 1, wherein the processor is further configured to determine a control quality value for the control data.

10. The system of claim 1, wherein the processor is further configured to determine a sample quality value for the sample data.

11. The system of claim 4, wherein providing an event notification includes displaying an alert.

12. The system of claim 1, wherein the comparison of the intensity, relative intensity, or quality of the control data to the intensity, relative intensity, or quality of the sample data comprises comparing an intensity of the control data to an intensity of the sample data.

13. The system of claim 1, wherein the comparison of the intensity, relative intensity, or quality of the control data to the intensity, relative intensity, or quality of the sample data comprises comparing a relative intensity of the control data to a relative intensity of the sample data.

14. The system of claim 1, wherein the comparison of the intensity, relative intensity, or quality of the control data to the intensity, relative intensity, or quality of the sample data comprises comparing a quality of the control data to a quality of the sample data.

15. The system of claim 14, wherein the quality of each of the control data and the sample data being compared comprises a probability that the data is not a result of a random or chance event or otherwise false.

16. A computer program product, comprising a non-transitory computer-readable storage medium whose contents include a program with instructions being executed on a processor, the instructions comprising:
   instructions to obtain control data for a control set comprising a collection of differing nucleic acids each having a known sequence and known physical properties and sample data for a nucleic acid sample from a sequencing instrument, instructions to determine a control quality value for the control data and a sample quality value for the sample data;

instructions to compare the control quality value and the sample quality value;

instructions to perform an event handling routine in response to determining that the control quality value or the sample quality value is below a threshold;

instructions to determine a required amount of a reagent needed by a sequencing instrument to sequence the nucleic acid sample;

instructions to determine an available amount of the reagent;

instructions to identify a time at which the sequencing instrument will need an additional amount of the reagent in response to determining that the required amount exceeds the available amount;

instructions to notify an operator of the time at which the sequencing instrument will need an additional amount of the reagent;

instructions to notify the sequencing instrument to suspend interrogating the nucleic acid sample prior to the time at which the sequencing instrument will need the additional amount of the reagent; and instructions to notify the sequencing instrument to resume interrogating the nucleic acid sample in response to determining that the additional amount of the reagent has been added.

17. The computer program product of claim 16, further comprising instructions to generate a graphical representation of the sample quality value.

18. The computer program product of claim 16, wherein instructions to perform the event handling routine include instructions to provide an event notification.

19. The computer program product of claim 18, wherein instructions to provide an event notification includes instructions to send an electronic message, instructions to display an alert, or any combination thereof.

20. The computer program product of claim 18, wherein the instructions to provide an event notification include instructions to provide an explanation of the probable cause of the event condition based on comparing the control quality value, the sample quality value, and the threshold.

* * * * *